US009039992B2

(12) United States Patent
Fritchie

(10) Patent No.: US 9,039,992 B2
(45) Date of Patent: May 26, 2015

(54) APPARATUS FOR CLOSED TUBE SAMPLING AND OPEN TUBE SAMPLING FOR AUTOMATED CLINICAL ANALYZERS

(75) Inventor: Patrick P. Fritchie, Southlake, TX (US)

(73) Assignee: ABBOTT LABORATORIES, Abbott Park, IL (US)

( * ) Notice: Subject to any disclaimer, the term of this patent is extended or adjusted under 35 U.S.C. 154(b) by 335 days.

(21) Appl. No.: 13/154,147

(22) Filed: Jun. 6, 2011

(65) Prior Publication Data

US 2012/0308435 A1    Dec. 6, 2012

(51) Int. Cl.
| | | |
|---|---|---|
| *B04B 5/02* | (2006.01) | |
| *C12Q 1/68* | (2006.01) | |
| *G01N 9/30* | (2006.01) | |
| *G01N 21/75* | (2006.01) | |
| *B04B 5/04* | (2006.01) | |
| *B04B 9/14* | (2006.01) | |
| *B04B 11/04* | (2006.01) | |
| *G01N 35/00* | (2006.01) | |

(52) U.S. Cl.
CPC .............. *B04B 5/0421* (2013.01); *B04B 9/146* (2013.01); *B04B 11/04* (2013.01); *B04B 2011/046* (2013.01); *G01N 2035/00504* (2013.01)

(58) Field of Classification Search
CPC   B04B 11/04; B04B 2011/046; B04B 5/0421; B04B 9/146
USPC ........... 494/16, 20, 22; 422/50, 72, 415, 550, 422/918
See application file for complete search history.

(56) References Cited

U.S. PATENT DOCUMENTS

| | | | | |
|---|---|---|---|---|
| 3,712,535 A | * | 1/1973 | Genese et al. | 494/17 |
| 3,935,995 A | * | 2/1976 | Williams et al. | 494/20 |
| 4,010,893 A | * | 3/1977 | Smith et al. | 494/1 |
| 4,116,635 A | | 9/1978 | Jaeger | |
| 4,669,321 A | | 6/1987 | Meyer | |

(Continued)

FOREIGN PATENT DOCUMENTS

| | | |
|---|---|---|
| EP | 0224955 | 6/1987 |
| EP | 0390848 B1 | 4/1998 |

(Continued)

OTHER PUBLICATIONS

Accelerometer [online], [retrieved on Aug. 2, 2011]. Retrieved from the Internet:< URL: http://en.wikipedia.org/wiki/Accelerometer>.

(Continued)

*Primary Examiner* — Dean Kwak
(74) *Attorney, Agent, or Firm* — Hanley, Flight & Zimmerman LLC

(57) ABSTRACT

A centrifuge to which sample tubes can be introduced while the centrifuge is in motion. The centrifuge comprises a carousel having an upper portion and a lower portion. The upper portion of the carousel has a plurality of positions for sample tubes for a centrifugation operation, a plurality of drive mechanisms attached to the upper portion of the carousel, a movable element mounted upon each drive mechanism, the movable element capable of traversing the length of the drive mechanism when the drive mechanism is actuated, a sample tube-holding assembly comprising a sample tube holder and a bearing attached to each movable element, and at least one balancing element capable of contributing to a force vector that cancels an imbalance vector generated by rotation of the centrifuge.

66 Claims, 19 Drawing Sheets

(56) References Cited

U.S. PATENT DOCUMENTS

| | | | |
|---|---|---|---|
| 4,756,201 A | | 7/1988 | Uffenheimer |
| 4,769,000 A | | 9/1988 | Van Heel |
| 4,799,393 A | | 1/1989 | Uffenheimer |
| 4,811,611 A | | 3/1989 | Uffenheimer |
| 5,130,254 A | | 7/1992 | Collier et al. |
| 5,201,232 A | | 4/1993 | Uffenheimer |
| 5,216,926 A | | 6/1993 | Lipscomb |
| 5,584,790 A | * | 12/1996 | Bell et al. ............ 494/20 |
| 5,588,946 A | * | 12/1996 | Graham et al. ........... 494/11 |
| 5,728,954 A | | 3/1998 | Uffenheimer |
| 5,767,381 A | * | 6/1998 | Konno et al. ............. 73/1.87 |
| 5,841,039 A | | 11/1998 | Uffenheimer |
| 6,033,355 A | | 3/2000 | Smith et al. |
| 6,060,022 A | | 5/2000 | Pang et al. |
| 6,234,948 B1 | * | 5/2001 | Yavilevich ............ 494/20 |
| 6,475,801 B1 | | 11/2002 | Nishizaki et al. |
| 6,627,156 B1 | | 9/2003 | Goodale et al. |
| 6,776,961 B2 | | 8/2004 | Lindsey et al. |
| 6,809,076 B2 | | 10/2004 | Scherhag et al. |
| 7,141,213 B1 | | 11/2006 | Pang et al. |
| 7,458,483 B2 | | 12/2008 | Luoma, II |
| 7,510,684 B2 | | 3/2009 | Goodale et al. |
| 7,662,339 B2 | | 2/2010 | Mattila et al. |
| 7,678,331 B2 | | 3/2010 | Shanafelter |
| 8,038,942 B2 | | 10/2011 | Pang et al. |
| 2002/0015665 A1 | | 2/2002 | Lindsey et al. |
| 2002/0110491 A1 | | 8/2002 | Goodale et al. |
| 2004/0020310 A1 | * | 2/2004 | Escal ................ 73/864.21 |
| 2006/0088443 A1 | | 4/2006 | Mattila et al. |
| 2006/0252627 A1 | * | 11/2006 | Kim et al. ............ 494/20 |
| 2007/0004577 A1 | * | 1/2007 | Lederer ............... 494/20 |
| 2008/0024301 A1 | | 1/2008 | Fritchie et al. |
| 2009/0036764 A1 | * | 2/2009 | Rivas et al. ............ 600/365 |
| 2009/0136383 A1 | | 5/2009 | Goodale et al. |
| 2010/0009833 A1 | | 1/2010 | Ryu et al. |
| 2012/0302419 A1 | | 11/2012 | Ryu et al. |

FOREIGN PATENT DOCUMENTS

| | | |
|---|---|---|
| IT | TO2011A000009 | 4/2011 |
| JP | 52087760 | 7/1977 |
| JP | 2010064012 | 3/2010 |

OTHER PUBLICATIONS

Balancing Machine [online], [retrieved on Apr. 27, 2011]. Retrieved from the Internet:< URL: http://en.wikipedia.org/wiki/Balancing_machine>.

BD Diagnostics—Preanalytical Systems, BD Vacutainer [online], [retrieved on Jan. 25, 2011]. Retrieved from the Internet:< URL: http://www.bd.com/vacutainer/products/venous/plus_plastic_tubes_docs.asp>.

Cell-Dyn Sapphire. Abbott Diagnostics Products [online], Abbott Laboratories, 2008 [retrieved on Nov. 25, 2007]. Retrieved from the Internet: <URL:http://www.abbottdiagnostics.corn/Products/Instruments_by_Platform/default.cfm?system=CELLDYN& suffix=Sapphir.

Central Processing Unit, From Wikipedia, the free encyclopedia [retrieved on Feb. 16, 2011]. Retrieved from the Internet:< URL: http://en.Wikipedia.org/wiki/Central_Processing_Unit>.

Centrifuge [online], [retrieved on Feb. 16, 2011]. Retrieved from the Internet:< URL: http://en.wikipedia.org/wiki/Centrifuge>.

Clinical Chemistry, From Wikipedia, the free encyclopedia [retrieved on Nov. 18, 2010]. Retrieved from the Internet:< URL: http://en.Wikipedia.org/wiki/Clinical_Chemistry>.

Eagle Tree Systems, Instruction manual for the Optical RPM Sensor, Document Version 2.2. Retrieved from the Internet:< URL: http://www.eagletreesystems.com>.

Hematology, From Wikipedia, the free encyclopedia [retrieved on Feb. 15, 2011]. Retrieved from the Internet:< URL:http://en.Wikipedia.org/wiki/Hematology>.

Immunoassay, From Wikipedia, the free encyclopedia [retrieved on Nov. 18, 2010]. Retrieved from the Internet:< URL: http://en.Wikipedia.org/wiki/Immunoassay>.

K&J Magnetics., Inc., BX8X8X8-N52 [online], [retrieved on Feb. 8, 2011]. Retrieved from the Internet:< URL: http://www.kjmagnetics.com/proddetail.asp?prod=BX8X8X8%DN52>.

K&J Magnetics., Inc., D44-N52 [online], [retrieved on Feb. 8, 2011]. Retrieved from the Internet:< URL: http://www.kjmagnetics.com/proddetail.asp?prod=D44%02DN52>.

Lantec—SRB-N21.9-0.83 Ring Bearing [online], [retrieved on Feb. 8, 2011]. Retrieved from the Internet:< URL: http://www.globalspec.com/FeaturedProducts/Detail/Lantec/SRBN219083_Ring_Bearing/1 . . . >.

Low Profile Uni-Guide [online], [retrieved on Feb. 8, 2011]. Retrieved from the Internet:< URL: http://www.pbclinear.com/Low-Profile-Uni-Guide>.

McCall R.E., et al., "Computers and Specimen Handling and Processing" in: Phlebotomy Essentials, 4th Edition (Chapter 14), Lippincott Williams & Wilkins, 2008, pp. 521-522.

Miniature Inch Ball Bearings (Radial, Flanged & Extended Inner) [online], [retrieved on Feb. 8, 2011]. Retrieved from the Internet:< URL: http://www.impactbearing.com/miniature_bearing_instrument.html>.

Peek (polyetheretherketone) Tubing [online], [retrieved on Jun. 1, 2011]. Retrieved from the Internet:< URL: http://www.coleparmer.com/catalog/product_index.asp?cls=6808>.

Simon, et al., The Way Thing Work, vol. 2, Simon & Schuster, 1971, pp. 506-517.

Torsion Springs [online], [retrieved on Feb. 8, 2011]. Retrieved from the Internet:< URL: http://wvvw.leespring.com/int_learn_torsion.asp>.

Venipuncture, From Wikipedia, the free encyclopedia [retrieved on May 7, 2011]. Retrieved from the Internet:< URL: http://en.Wikipedia.org/wiki/Venipuncture>.

Venous Products, BD Vacutainer Tubes, Table of Contents.

Vibration Sensors [online], [retrieved on Feb. 8, 2011]. Retrieved from the Internet:< URL: http://wvvw.hofmann-balancing.com/products/vibration-sensors.html>.

Vishay Semiconductors, "Reflective Optical Sensor with PIN Photodiode Output," TCND5000, 2010.

Vision Control Suite [online], [retrieved on Jun. 1, 2011]. Retrieved from the Internet:< URL: http://www.jadaktech.com/products/machine_vision/MVCS.html>.

International Searching Authority, "Invitation to Pay Additional Fees and Partial International Search," issued in connection with international application No. PCT/US2012/040840, on Oct. 25, 2012 (8 pages).

International Searching Authority, "International Search Report and Written Opinion," issued in connection with PCT application PCT/US12/40840, on Feb. 6, 2013 (18 pages).

International Bureau, "International Preliminary Report on Patentability," issued in connection with application No. PCT/US2012/040840, on Dec. 10, 2013, 11 pages.

* cited by examiner

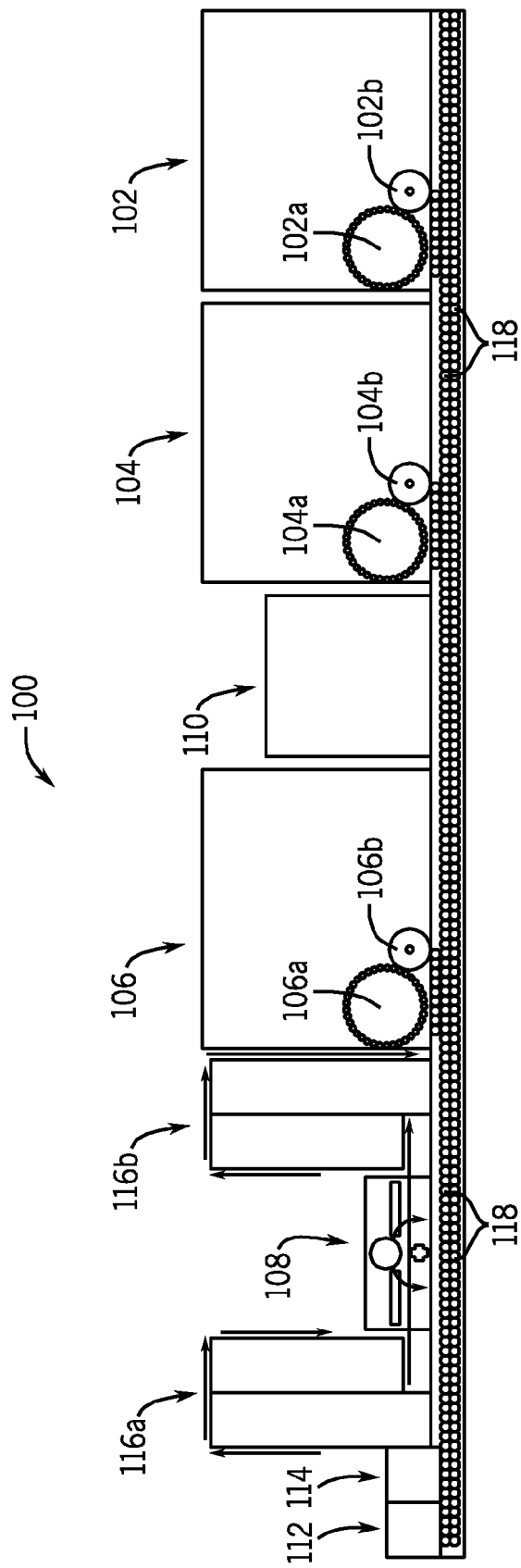

APPARATUS FOR CLOSED TUBE SAMPLING AND OPEN TUBE SAMPLING FOR AUTOMATED CLINICAL ANALYZERS

BACKGROUND OF THE INVENTION

1. Field of the Invention

This invention involves a system for preparing biological samples for automated diagnostic analyses.

2. Discussion of the Art

A centrifuge is a piece of equipment that puts an object in rotation around a fixed axis, applying a force perpendicular to the axis. A centrifuge is generally driven by an electric motor. The centrifuge works using the sedimentation principle, where the centripetal acceleration causes more dense substance to separate out along the radial direction (the bottom of the tube). Simultaneously, lighter objects will tend to move to the top of the tube.

Protocols for centrifugation typically specify the amount of acceleration to be applied to the sample, rather than specifying a rotational speed such as revolutions per minute. This distinction is important because two rotors with different diameters running at the same rotational speed will subject samples to different accelerations. During circular motion the acceleration is the product of the radius and the square of the angular velocity and it is traditionally named "relative centrifugal force" (RCF). The acceleration is measured in multiples of "g" (or ×"g"), the standard acceleration due to gravity at the earth's surface, and it is given by $$RCF = r(2\pi N)^2/g$$

where g represents the earth's gravitational acceleration,
r represents the rotational radius, and
N represents the rotational speed, measured in revolutions per unit of time.
The relationship may be written as $$RCF = 1.118 \times 10^{-5} r_{cm} N^2_{RPM}$$

where $r_{cm}$ represents the rotational radius measured in centimeters,
$N_{RPM}$ represents the rotational speed measured in revolutions per minute (RPM)
$g = (980.65\ cm/sec^2)(3600\ sec^2/minute^2) = 3{,}530{,}340\ cm/minute^2$ Clinical chemistry is the area of pathology that is generally concerned with analysis of body fluids. The discipline originated in the late nineteenth century with the use of simple chemical tests for various components of blood and urine. Subsequently other techniques were applied including the use and measurement of enzyme activities, spectrophotometry, electrophoresis, and immunoassay. Most current laboratories are not highly automated and use assays that are monitored closely and controlled for quality. Tests that require examination and measurement of the cells of blood, as well as blood clotting studies, are not included, as they are generally grouped under hematology. Clinical chemistry tests can be performed on any kind of body fluid, but are generally performed on serum or plasma. Serum is the yellow watery part of blood that is left after blood has been allowed to clot and all blood cells have been removed. Such removal is most easily done by centrifugation, which packs the denser blood cells and platelets to the bottom of the centrifuge tube, leaving the liquid serum fraction resting above the packed cells. Plasma is essentially the same as serum, but is obtained by centrifuging the blood without clotting. Plasma therefore contains all of the clotting factors, including fibrinogen.

An immunoassay is a biochemical test that measures the presence or concentration of a substance in solutions that frequently contain a complex mixture of substances. Analytes in biological liquids such as serum or urine are frequently assayed using immunoassay methods. Such assays are based on the unique ability of an antibody to bind with high specificity to one or a very limited group of molecules. A molecule that binds to an antibody is called an antigen. Immunoassays can be carried out for either member of an antigen/antibody pair. For antigen analytes, an antibody that specifically binds to that antigen can frequently be prepared for use as an analytical reagent. When the analyte is a specific antibody, its cognate antigen can be used as the analytical reagent. In either case the specificity of the assay depends on the degree to which the analytical reagent is able to bind to its specific binding partner to the exclusion of all other substances that might be present in the sample to be analyzed. In addition to the need for specificity, a binding partner must be selected that has a sufficiently high affinity for the analyte to permit an accurate measurement. The affinity requirements depend on the particular assay format that is used.

In addition to binding specificity, the other key feature of all immunoassays is a means for producing a measurable signal in response to a specific binding. Historically, the signal involved measuring a change in some physical characteristic such as light scattering or changes in refractive index. Most immunoassays today depend on the use of an analytical reagent that is associated with a detectable label. A large variety of labels have been demonstrated including radioactive elements used in radioimmunoassay; enzymes; fluorescent, phosphorescent, and chemiluminescent dyes; latex and magnetic particles; dye crystallites, gold, silver, and selenium colloidal particles; metal chelates; coenzymes; electroactive groups; oligonucleotides, stable radicals and others. Such labels serve for detection and quantitation of binding events either after separating free and bound labeled reagents or by designing the system in such a way that a binding event effects a change in the signal produced by the label. Immunoassays requiring a separation step, often called separation immunoassays or heterogeneous immunoassays, are popular because they are easy to design, but they frequently require multiple steps including careful washing of a surface onto which the labeled reagent has bound. Immunoassays in which the signal is affected by binding can often be run without a separation step. Such assays can frequently be carried out simply by mixing the reagents and sample and making a physical measurement. Such assays are called homogeneous immunoassays or less frequently non-separation immunoassays.

Regardless of the method used, interpretation of the signal produced in the immunoassay requires reference to a calibrator that mimics the characteristics of the sample medium. For qualitative assays the calibrators may consist of a negative sample with no analyte and a positive sample having the lowest concentration of the analyte that is considered detectable. Quantitative assays require additional calibrators with known analyte concentrations. Comparison of the assay response of a real sample to the assay responses produced by the calibrators makes it possible to interpret the signal strength in terms of the presence or concentration of analyte in the sample.

Hematology is the branch of internal medicine, physiology, pathology, clinical laboratory work, and pediatrics that is concerned with the study of blood, the blood-forming organs, and blood diseases. Hematology includes the study of etiology, diagnosis, treatment, prognosis, and prevention of blood diseases. The laboratory work that does into the study of blood is frequently performed by a medical technologist. Blood diseases affect the production of blood and its components, such as blood cells, hemoglobin, blood proteins, the mechanism of coagulation, etc.

Hematology tests include a wide variety of laboratory studies, ranging from coagulation factors to various cell evaluations. A sample of whole blood is taken, usually from a vein. Amounts differ according to the number and types of tests to be run and the testing instruments to be used. Typically red blood cells are counted and lysed (broken down); then white blood cells are measured. Because blood clots quickly, the measured blood sample is diluted with either a lysing agent or an anti-clotting agent, depending on the test(s) to be completed. A lysing agent breaks down the red blood cells and allows counting of white blood cells. Dilution is an important step in preparing samples for testing for several reasons. First, concentrations of the anticoagulant must be adequate for the volume of blood. Insufficient dilution may allow formation of small clots that lower cell counts; excessive dilution can cause cells to shrink or swell. Anticoagulants that are widely used are EDTA (ethylenediaminetetraacetic acid) and heparin. EDTA is used often for routine cell counts and platelet counts. Heparin inhibits clotting without distorting red blood cell volume and is the preferred anticoagulant for studies of leukocytes. Second even relatively large blood samples do not provide a sufficient quantity to flow through an analyzer for measurement. Blood must be mixed with a diluent that will allow the cells to be evenly suspended in sufficient liquid to flow at a constant rate for measurement. Counts and other tests should be run within three to four hours of obtaining blood samples (within one to two hours for platelet counts).

Automated hematology has been used in large laboratories for many years. Automated technologies include the following:

1. Impedance principle: This is the coulter principle based on the fact that blood cells are poor conductors of electricity. Coulter counters count cells as they flow, in single file, through an aperture in an electric field. As each cell crosses the aperture, the increase in electrical impedance is proportional to the cell's size. The cells are uniformly suspended in a diluent, and the suspension passes through the aperture at a constant rate. Because these counters discriminate between particles according to size, their thresholds (usually aperture size) can be set to the preferred size limit, depending on the cells to be counted. Dilutions for white blood cell count are critical. Because these cells are small and numerous, samples with high white blood cell counts may exceed the counting capacity of the instrument or may cause high coincidence counts—that is counts in which two cells pass through the aperture simultaneously. An increased amount of diluent may be needed to avoid these errors, or an instrument may automatically correct for these errors.
2. Optical principles: Automated systems are based on flow-through (also called flow cytometer) optical technologies that identify cells on the basis of their fluorescent labeling ability. Blood cells in a diluent pass through an aperture, scattering a focused light beam. Cells diffract (scatter) light in a manner that is measurable and unique to each cell type. Accuracy can be influenced by coincidence errors—two cells passing through the aperture may be measured as one large cell (primary coincidence) or two particles that are below the measurement threshold may be counted as one cell (secondary coincidence). In most cases, the coincidence factor is too small to distort the count significantly. Most instruments automatically correct for coincidence errors.

Automated analyzers for clinical chemistry that are commercially available include those sold under the trademarks "ARCHITECT" c16000, "ARCHITECT" c4000, and "ARCHITECT" c8000, all of which are commercially available from Abbott Laboratories, Abbott Park, Ill. Automated analyzers for immunoassays that are commercially available include those sold under the trademarks "ARCHITECT" i1000SR, "ARCHITECT" i2000SR, "ARCHITECT" i4000SR, and "AxSYM", all of which are commercially available from Abbott Laboratories, Abbott Park, Ill. Automated analyzers for hematology that are commercially available include those sold under the trademarks "CELL-DYN" 1800, "CELL-DYN" 3200, and "CELL-DYN" 3700, all of which are commercially available from Abbott Laboratories, Abbott Park, Ill.

Automated analyzers for clinical chemistry, automated analyzers for immunoassays, and automated analyzers for hematology typically require one or more of the following components:

(a) Piercing station, where stoppers of sample tubes are penetrated to enable a sample aspirating probe to aspirate a portion of the sample;
(b) Automated system for transporting samples for moving samples from one automated analyzer to another, thereby integrating automated analyzers;
(c) Aspirating/dispensing devices for removing samples from sample tubes and dispensing samples into reaction vessels;
(d) Blood separation device for separating blood cells from plasma after a sample of whole blood has been withdrawn from a sample container;
(e) Decapping devices for removing caps from sample containers.

U.S. Pat. No. 6,033,355 describes a centrifuge having a plurality of individual centrifuge devices and a robotic loading and/or unloading device. Each of the centrifuge devices may be loaded and unloaded without affecting the operation of the other centrifuge devices. The centrifuge devices include a plurality of rotors that re spaced apart and translated along a predetermined path. The rotors are rotatably mounted with respect to the predetermined path and the rotational planes of the rotors extend substantially at right angles to the predetermined path.

Several other types of whole blood separation techniques are available, such as, for example, batch type centrifugation and serum filters.

Testing blood samples in a laboratory exposes operators to biological hazards, including aerosols. In addition, when operators remove stoppers from closed sample tubes, repetitive motion can lead to physical injuries, such as carpal tunnel syndrome. It would be desirable to develop a system to reduce these risks to the operators without reducing throughput and assay performance. It would also be desirable to reduce exposure of operators to cutting "sharps" hazards.

Laboratories that test blood samples expend substantial labor to sort sample tubes for hematology or immunoassay/clinical chemistry testing. In addition to this sorting, balancing and centrifugation is performed on sample tubes destined for immunoassay/clinical chemistry testing. These operations add a minimum of 10 minutes or more to time needed to obtain a result, and could delay an assay of a STAT sample by an additional 10 minutes. Integration of hematology/immunoassay/clinical chemistry testing would reduce the labor required for sorting, balancing, and centrifugation and significantly reduce the time needed to obtain a result by integrating the blood separation step into the analyzer system/work cell. It would be desirable to provide a fully automated method for processing one sample tube for hematology/immunoassay/clinical chemistry testing, while providing high throughput for large laboratories that process many samples, and random and continuous access assay processing, as well as analysis of STAT samples. In addition, it would be desirable to realize these benefits with the current product lines without requiring new analyzers to be developed. It would be desirable to develop systems for use in a variety of customer environments, e.g., laboratories, with minimal changes.

Patients and phlebotomists are required to provide two sample tubes for hematology testing and immunoassay/clinical chemistry testing. The integration of hematology/immunoassay/clinical chemistry testing would reduce patient distress, reduce cost of collecting samples, reduce cost of inventory (to stock more than one type of sample tube), and reduce cost of disposal of solid waste.

Designs for centrifuge have typically been "batch" type designs, requiring all sample tubes to be loaded and then separated for 10 minutes (at minimum). If a STAT sample arrives just after the centrifugation process begins, the STAT sample would be delayed 10 minutes (at minimum). A continuous access centrifuge would eliminate "batches", and any subsequent delays for processing STAT samples, thereby reducing the time required for centrifugation to five (5) minutes.

Designs for centrifuge have typically been targeted for laboratories in developed countries, where electrical power, air conditioning, etc., are commonplace. A continuous access centrifuge would provide the ability receive energy from sources other than electrical, such as hand cranks, bicycles, windmills, waterwheels, etc., thereby allowing modern centrifugation techniques to be performed in developing countries.

Testing blood samples in a laboratory requires a substantial amount of labor to sort sample tubes for hematology testing, immunoassay testing, or clinical chemistry testing. In addition to this sorting, balancing and centrifugation is carried out for sample tubes destined for immunoassay testing and clinical chemistry testing. Balancing and centrifugation adds a minimum of 10 minutes or more to time needed to obtain a result.

SUMMARY OF THE INVENTION

In one aspect, this invention provides a novel centrifuge. In any of the embodiments, sample tubes can be introduced into the centrifuge while the centrifuge is in motion. In all of the embodiments, the centrifuge comprises a carousel having an upper portion and a lower portion. The upper portion of the carousel has a plurality of positions for sample tubes for a centrifugation operation, a plurality of drive mechanisms attached to the upper portion of the carousel, a movable element mounted upon each drive mechanism, the movable element capable of traversing the entire length of the drive mechanism or any portion thereof when the drive mechanism is actuated, a sample tube-holding assembly comprising a sample tube holder and a bearing attached to each movable element, and at least one balancing element capable of contributing to a force vector that cancels an imbalance vector generated by rotation of the centrifuge. The lower portion of the carousel includes the rotor coils and field coils for bringing about movement of the carousel itself.

The force vector is of such a magnitude and direction as to cancel any imbalance(s) created by the sample tubes and the sample tube holders, while taking into account the distances of the various sample tubes from the axis of the carousel of the centrifuge.

In one embodiment, the centrifuge comprises an exterior balancing cap and an interior balancing cap. The exterior balancing cap and the interior balancing cap, which are concentric, can be rotated about the axis of rotation of the carousel of the centrifuge. Each of the exterior balancing cap and the interior balancing cap comprises a platform that covers the upper portion of the carousel and a skirt depending from the platform, the skirt being perpendicular to the platform of the balancing cap.

In another embodiment, a balancing weight is used to balance the centrifuge. The balancing weight is attached to and supported by a first positioning mechanism, and the combination of the balancing weight and the first positioning mechanism is further attached to and supported by a second positioning mechanism, the second positioning mechanism supported by the carousel of the centrifuge. The positioning mechanisms can be moved in the appropriate directions to move the balancing weight to cancel any imbalance generated by rotation of the centrifuge.

In still another embodiment, the centrifuge comprises an assembly comprising at least three balancing elements. The three balancing elements can be moved to cancel any imbalance generated by rotation of the centrifuge. Each balancing element comprises a balancing nut that can be moved along a lead screw. The first lead screw rotates within a first bearing, the second lead screw rotates within a second bearing, and the third lead screw rotates within a third bearing. The first lead screw is actuated by a stepper motor positioned at the end of the first lead screw opposite to the end where the bearing is positioned, the second lead screw is actuated by a stepper motor positioned at the end of the second lead screw opposite to the end where the bearing is positioned, and the third lead screw is actuated by a stepper motor positioned at the end of the third lead screw opposite to the end where the bearing is positioned.

In another aspect, this invention provides a system for integrating clinical chemistry analyzers, immunoassay analyzers, and hematology analyzers, or any combination of the foregoing. In one embodiment, the system comprises at least one clinical analyzer and the centrifuge described previously. The clinical analyzer can comprise at least one immunoassay analyzer. Alternatively, the clinical analyzer can comprise at least one clinical chemistry analyzer. In another alternative, the clinical analyzer can comprise at least one hematology analyzer. In still another alternative, the system can comprise any combination of at least one immunoassay analyzer, at least one clinical chemistry analyzer, and at least one hematology analyzer.

In still another aspect, this invention provides a system that can accommodate open-tube sampling and closed-tube sampling. When immunoassay analyzers and clinical chemistry analyzers are integrated with hematology analyzers, sample tubes must be loaded with stoppers in place (closed-tube system), because the hematology analyzer mixes the entire sample of blood by inverting the tube several times, thereby ensuring uniform distribution of blood cells. Subsequent to aspirating a sample for a hematology analysis, aliquots can be drawn from the closed tube and subsequently routed to a centrifuge and then to appropriate immunoassay analyzers and clinical chemistry analyzers for analysis. If immunoassay analyzers and clinical chemistry analyzers are not integrated with hematology analyzers, the sample tubes can be "open" or "closed". If sample tubes are "open" (stopper is removed), then all aliquots are withdrawn in the same manner as with the current "ARCHITECT" analyzers. If sample tubes are "closed" (stopper is in place), then either the stopper is penetrated at a piercing station and the sample tubes subsequently routed to analyzers for withdrawing of samples, or aliquots are withdrawn from the closed tube and subsequently routed to immunoassay analyzers and clinical chemistry analyzers for analysis.

The system described herein provides two options for aspirating a biological sample from a sealed sample tube. In the first option, the stopper of the sample tube is slit, thereby allowing standard sample aspirating probes on automated clinical analyzers to enter the stopper through a vent tube and aspirate the sample. In the second option, a sample aspirating probe typically used with an automated hematology analyzer pierces the stopper of the sample tube, aspirates the sample, and dispenses a portion of the sample into an open tube for subsequent use by automated clinical analyzers.

The system utilizes a common anti-coagulant so that a sample tube suitable for use by an automated hematology analyzer can also be used with an automated immunoassay analyzer and an automated clinical chemistry analyzer. Prior to analysis, any of several techniques for separating components of samples of whole blood can be employed. For example, components of samples of whole blood can be separated means of standing waves provided by ultrasonic energy or by means of magnetic particles coated with agglutinating reagent.

The system described herein provides various levels of automatically processing samples from sealed sample tubes and integrating hematology analyzers, Immunoassay analyzers, and clinical chemistry analyzers. Systems can be designed to meet needs of customers. Thus, systems can be enhanced or simplified to perform the functions desired.

The system described herein reduces risks to operators, without reducing throughput, assay performance, and without exposing the operators to cuts brought about by cutting openings in stoppers of sample tubes. Such risks include, but are not limited to, repetitive motion injury, exposure to biological hazards, and exposure to aerosols.

The integration of hematology testing, immunoassay testing, and clinical chemistry testing reduces the labor required for sorting, balancing, and centrifugation and significantly reduces the time needed to obtain a result by integrating the step for separating blood into the system containing the clinical analyzers. The system described herein provides a fully automated method for processing one sample in one sample tube that can be used for hematology testing, immunoassay testing, and clinical chemistry testing, while providing high throughput for large laboratories that process large numbers of samples, employ random and continuous access assay processing, as well as assays for STAT samples. In addition, these benefits can be realized with the current hematology analyzers, immunoassay analyzers, and clinical chemistry analyzers, such as, for example, "ARCHITECT" immunoassay analyzers, "ARCHITECT" clinical chemistry analyzers, and "CELL-DYN" hematology analyzers, without requiring the development of new analyzers. The system provides a variety of concepts for designing various laboratory environments without requiring significant changes.

Integration of hematology, immunoassay, clinical chemistry testing requires only one sample tube for testing, thereby reducing distress to the patient, the cost of collecting samples, the cost of inventory (to stock more than one type of sample tube), and the cost of disposing of solid waste.

The continuous access feature of the centrifuge described herein eliminates delays due to "batches", and consequently, any subsequent delays for processing STAT samples.

The continuous access centrifuge described herein enables the centrifuge to receive energy from mechanical sources, such as hand cranks, bicycles, windmills, waterwheels, etc., thereby allowing modern centrifugation steps to be carried out in developing countries.

BRIEF DESCRIPTION OF THE DRAWINGS

Except for FIGS. 8, 10, and 14, all of the drawings are schematic diagrams.

FIG. 9 is a schematic diagram illustrating a top plan view of a system employing a module for cutting slits into stoppers of sample tubes for use with an automated immunoassay analyzer and an automated clinical chemistry analyzer. FIG. 9 also shows a module for at least one immunoassay analyzer, a module for at least one clinical chemistry analyzer, a module for at least one hematology analyzer, and a module for at least one centrifuge or other equipment for separating components of a sample. It should be noted that one or more of the modules can be removed from the system, depending upon the requirements of the laboratory.

FIG. 15A is a side view illustrating a sample tube in the load/unload position of the centrifuge. FIG. 15B is a side view illustrating the sample tube of FIG. 15A tilted at an angle of 45° in the centrifuge. FIG. 15C is a side view illustrating the sample tube of FIG. 15A tilted at an angle of 90° in the centrifuge. FIG. 15D is the same view as FIG. 15A, with the exception that an empty sample tube-holding assembly in the load/unload position of the centrifuge is shown.

DETAILED DESCRIPTION

Figure 1:
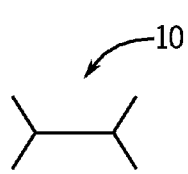
FIG. 1 is a bottom plan view of a cutting blade suitable for slitting a stopper of a sample tube.

In the drawings, insofar as possible, like parts have the same reference numeral.

As used herein, the expression "immunoassay analyzer" means an automated analyzer for determining the concentration of a substance in a sample by means of an immunoassay technique, i.e., a technique employing antibodies to search for antigens or a technique employing antigens to search for antibodies. There are three types of immunoassays: a direct sandwich assay, a competitive assay, or an antibody detection assay. These types of immunoassays are well-known to those having ordinary skill in the art. As used herein, the expression "clinical chemistry analyzer" means an automated analyzer for determining the concentration of a substance in a sample by means of a technique employing at least one chemical reaction. The chemical reaction can be an immunochemical reaction. As used herein, the expression "hematology analyzer" means an automated analyzer for determining various parameters of a sample of blood, namely counting of the components in a sample of blood and classification of the components in a sample of blood.

As used herein, the term "module" means a self-contained unit of a system that performs a specific task or class of tasks for supporting the major functions of the system. For example, a system of clinical analyzers can include, but is not limited to, some of the following modules: sample aspirating module, immunoassay analyzer, clinical chemistry analyzer, hematology analyzer, and centrifuge. A given module of the system is designed to be used with other modules of the system that are related thereto.

As used herein, the expression "reaction vessel" means a container in which a biochemical reaction is carried out. As used herein, the expression "collection tube" means a tube in which a sample of liquid is collected. The liquid can be a biological fluid, such as, for example blood. As used herein, the expression "aliquot tube" means a tube containing an aliquot of a sample. An aliquot is a portion of a specimen, or sample, used for testing. Aliquots of specimens, or samples, are sometimes created when multiple tests are ordered on a single specimen, or sample, and the tests are performed on different instruments or in different areas of the testing department. Aliquots are prepared by transferring a portion of the specimen, or sample, into one or more tubes labeled with the same identification information as the specimen, or sample, tube. See McCall et al., *Phlebotomy Essentials*, Fourth Edition, Lippincott Williams & Wilkins (2008: Baltimore, Md., USA), pages 521-522, incorporated herein by reference. As used herein, the expression "sample tube" means a tube in which a sample is collected. The sample can be a biological sample, such as, for example, blood.

As used herein, the expression "central processing unit" means the portion of a computer system that carries out the instructions of a computer program, and is the primary element carrying out the computer's functions. The central processing unit carries out each instruction of the program in sequence, to perform the basic arithmetical, logical, and input/output operations of the system. During circular motion of a centrifuge, the acceleration is the product of the radius and the square of the angular velocity and it is traditionally named "relative centrifugal force" (alternatively referred to herein as "RCF"). The acceleration is measured in multiples of "g" (or ב"g"), the standard acceleration due to gravity at the Earth's surface, a dimensionless quantity given by the expression:

$$RCF = \frac{r(2\pi N)^2}{g}$$

where
g represents earth's gravitational acceleration,
r represents the rotational radius,
N represents the rotational speed, measured in revolutions per unit of time.

It should be noted that "relative centrifugal force" relates only to the force attributable to rotation of the centrifuge and does not relate to the gravitational force attributable to the earth.

As used herein, the expression "G Force" means force of gravity=$F_g$ (in Newtons)=mass (in kilograms)×9.8 meters/sec².

As used herein, the expression "STAT sample" means a sample that must be processed immediately.

As used herein, the symbol "(s)" following the name of an item indicates that one or more of the subject items is intended, depending upon the context.

As used herein, the symbol "/", also known as a virgule, indicates alternatives. For example, the expression "alternative 1 and/or alternative 2" is intended to mean "alternative 1" or "alternative 2" or "both alternative 1 and alternative 2". The expression "sleeve/collar" is intended to mean an item that can be referred to as either a "sleeve" or a "collar."

As used herein, the expression "open tube sampling" means employment of sample tubes not having a stopper covering the opening of the sample tube. As used herein, the expression "closed tube sampling" means employment of sample tubes having a stopper covering the opening of the sample tube. When immunoassay analyzers and clinical chemistry analyzers are integrated with hematology analyzers, sample tubes must be loaded with stoppers in place (closed-tube system), because the hematology analyzer mixes the entire sample of blood by inverting the tube several times, thereby ensuring uniform distribution of blood cells. Subsequent to aspirating a sample for a hematology analysis, aliquots can be drawn from the closed tube and subsequently routed to a centrifuge and then to appropriate immunoassay analyzers and clinical chemistry analyzers for analysis. If immunoassay analyzers and clinical chemistry analyzers are not integrated with hematology analyzers, the sample tubes can be "open" or "closed". If sample tubes are "open", then all aliquots are withdrawn in the same manner as with the current "ARCHITECT" clinical analyzers. If sample tubes are "closed" (stoppers are in place), then either the stopper is cut at a cutting station and the sample tube is subsequently routed to clinical analyzers for withdrawing of samples, or aliquots are withdrawn from the closed sample tube and the aliquot tubes are subsequently routed to clinical analyzers for analysis.

As used herein, the expression "vent needle" means a thin-walled tube suitable for creating an opening in the stopper of a sample tube and equalizing the pressure within the sample tube to that of the surrounding atmosphere. The vent needle also functions as a guide or a sheath to prevent a sample aspirating probe from contacting the stopper of a sample tube.

As used herein, the term "centrifuge" means a device comprising a compartment spun about a central axis to separate materials of different density or to simulate gravity with centrifugal force. As used herein, the term "carousel" means a revolving circular platform. With respect to centrifuges described herein, a carousel is a component of a centrifuge. As used herein, the expressions "axis of the carousel", "axis of rotation of the carousel", and the like, means a straight line about which the carousel rotates. The "axis of the carousel", "axis of rotation of the carousel", and the like, in effect, are synonymous with the central axis of the centrifuge. As used herein, the term "weight" means the gravitational force exerted by the earth on an object, equal to the product of the object's mass and the local value of gravitational acceleration. In general, the terms "weight" and "mass" are used interchangeably herein. As used herein, the expression "force" means a vector quantity that tends to produce an acceleration of a body in the direction of its application. As used herein, the expression "force vector" means the vector that characterizes a force that tends to produce an acceleration of a body in the direction of the application of the force.

Samples for hematology are typically whole blood. Samples for immunoassays and clinical chemistry assays are typically serum or plasma. After a sample of whole blood is aspirated from a sample tube, a portion of the sample of whole blood must be removed from the sample of whole blood so that either serum or plasma can be separated from the portion for subsequent use in immunoassay testing or clinical chemistry testing.

In the field of medicine, venepuncture, venopuncture or venipuncture is the process of obtaining intravenous access for the purpose of intravenous therapy or obtaining a sample of venous blood. This procedure is performed by medical laboratory scientists, medical practitioners, some emergency medical technicians, paramedics, phlebotomists and other nursing staff. Venepuncture is one of the most routinely performed invasive procedures and is carried out for two reasons, to obtain blood for diagnostic purposes or to monitor levels of blood components. Blood analysis is one of the most important diagnostic tools available to clinicians within healthcare. Its data is relied upon in the clinical setting for interpretation of a myriad of clinical signs and symptoms and developing skills in venepuncture can facilitate holistic and timely treatment.

Most blood collection in the United States and the United Kingdom is done with an evacuated tube system, (two common systems are "VACUTAINER" (Becton, Dickinson and Company) and "VACUETTE" (Greiner Bio-One GmBH). The equipment includes a plastic hub, a hypodermic needle, and a vacuum tube. Under certain circumstances, a syringe may be used, often with a butterfly needle, which is a plastic catheter attached to a short needle. In the developing world, a needle and syringe are still the most common method of drawing blood.

The tubes in which blood is transported to the laboratory contain a variety of additives or none at all. It is important to know which tube the individual laboratory requires for which test, because reagents vary among laboratories and may be affected by different additives. In general, whole blood needs to be mixed with EDTA, which chelates calcium to prevent it clotting, unless the clotting time is the test to be measured, in which case citrates are used. The majority of biochemistry tests are performed on serum, and, consequently, either a plain tube or a clotting accelerator is used. This clotting accelerator can interfere with some assays; accordingly, a plain tube is recommended in these cases, but the result will obviously be delayed the result. Some assays may also require whole blood but are interfered with by EDTA and in this case Lithium Heparin is a suitable alternative.

With the vacuum tube system, the needle pierces the stopper of the sample tube and will potentially come into contact with the additives in the tube. Because the needle is a hollow needle, some of the sample can be carried into the next tube and contaminate the contents thereof. The most likely additive to cause trouble is EDTA, which will affect coagulation time assays, and, by chelating some of the metal ions in the sample, may interfere with some of the biochemistry results (especially potassium). Thus EDTA samples should be drawn last in most cases and plain tubes drawn first.

Vacuum tubes were first marketed by Becton, Dickinson and Company under the trade name "VACUTAINER" tubes. Today, many companies sell vacuum tubes, because the patent for this device is in the public domain. Some models are a type of test tube that contains a vacuum that automatically aspirates blood into itself. The tubes are made of glass or plastic. The tubes are attached to a needle and hub.

Typical stoppers suitable for use with sample tubes can be seen by means of the Hypertext Transfer Protocol on the World Wide Web at the website bd.com/vacutainer/products/venous/plus_plastic_tubes_docs.asp, incorporated herein by reference. The catalog at the aforementioned website illustrates stoppers having various materials, shapes, means of attachment to a sample container, and dimensions. The stopper can be made from materials such as rubber or a synthetic polymeric material. The sample tube can be made from glass or a synthetic polymeric material. Tubes and stoppers suitable for use herein are commercially available from Becton, Dickinson and Company, Franklin Lakes, N.J.

Figure 2:
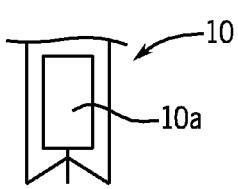
FIG. 2 is a side view of the cutting blade of FIG. 1.
Figure 3:
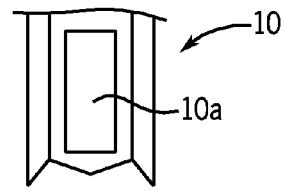
FIG. 3 is a front view of the cutting blade of FIG. 1.

FIGS. 1, 2, and 3 illustrate a cutting blade 10 capable of forming a slit in a stopper. The cutting blade 10 has a shape that can be characterized as an elongated cut having two ends, which elongated cut is disposed between a first cut that resembles the ")" symbol and a second cut that resembles the "(" symbol. One embodiment of the slit is shown below:

The angle between the two legs of the ")" symbol typically ranges from about 60° to about 120°, preferably 90°. The angle between the two legs of the "(" symbol typically ranges from about 60° to about 120°, preferably 90°. The vertex of the ")" symbol is in contact with one end of the elongated cut, and the vertex of the "(" symbol is in contact with other end of the elongated cut.

FIGS. 2 and 3 show that the cutting blade 10 has tip angles (center to outside, and outside to center) to control stretching of a stopper and promote efficient cutting of rubber and synthetic polymeric material. Further, the cutting blades 10 can be equipped with at least one groove 10a to retain a small, residual amount of wash buffer containing a detergent or a surfactant for lubrication. Prior to the cutting operation, the cutting blade 10 is washed. During the cutting operation, the cutting blade 10 is driven downward vertically, thereby cutting through the stopper of the sample tube. Prior to cutting the stopper, a detector for the stopper of the sample tube will ensure that a stopper is in place and that the stopper in place is the type that can be slit. Detectors that are suitable for this function are commercially available from JADAK Technologies, Syracuse, N.Y. By means of tube assist vision control software, such detectors can detect tube height, tube shape, cap presence or absence, cap shape. See, for example, the subject matter accessible by means of the Hypertext Transfer Protocol on the World Wide Web at the website jadaktech.com/products/machine_vision/MVCS.html, incorporated herein by reference. If a stopper is not present on a sample tube, or if the stopper of the sample tube is not of the type that can be slit, then the stopper of the sample tube will not be cut. A sample tube having the wrong type of stopper will not be processed.

Figure 4:
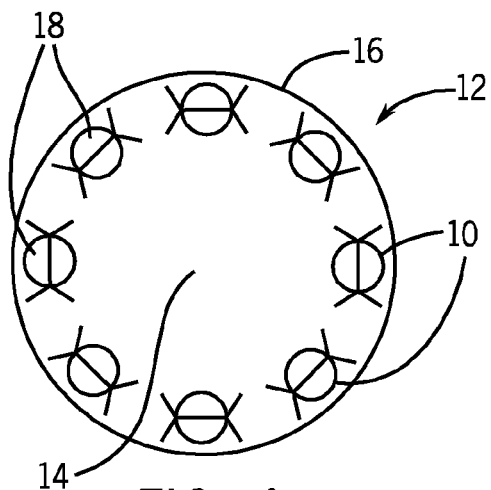
FIG. 4 is a bottom plan view of a holder for holding a plurality of devices that can be used in the sampling systems described herein. The devices that can be held include, but are not limited to, devices for cutting slits in stoppers, devices for piercing stoppers, and devices for expanding slits that have been cut in stoppers.
Figure 5:
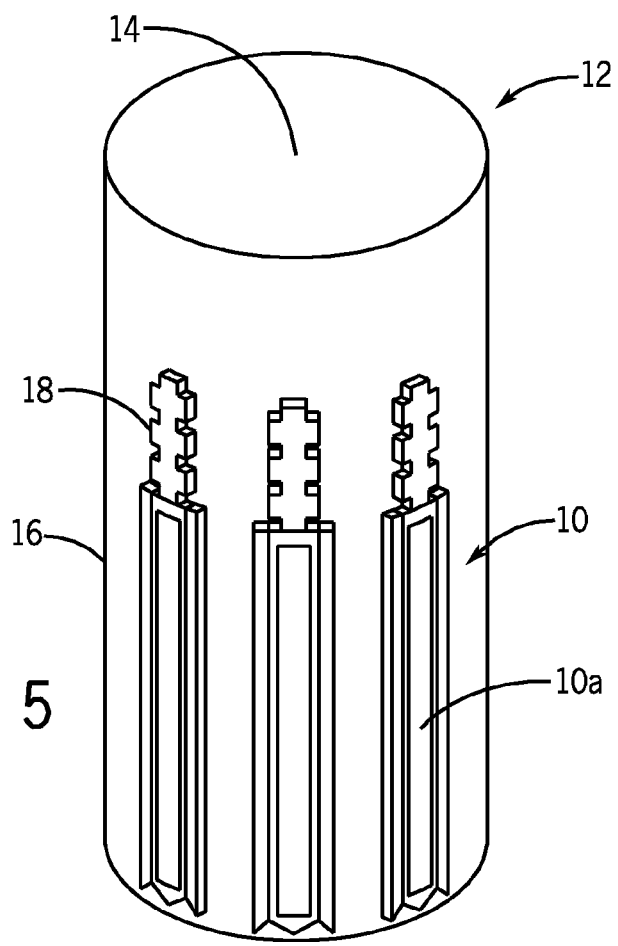
FIG. 5 is an isometric view of the holder of FIG. 4.

FIGS. 4 and 5 illustrate a holder 12 suitable for holding a plurality of cutting blades 10. The cutting blade holder 12 will rotate (index) one position clockwise (or counter-clockwise, if desired), the used cutting blade 10 will be rotated into one of seven (7) possible wash positions, and a washed cutting blade 10 will be positioned in the aspirating location, as the next sample tube is moved into position for aspiration. After a cutting blade 10 is used, it is washed to prevent contamination by carryover of the sample. In order to minimize reduction of throughput on account of washing of the cutting blade 10, the cutting blade holder 12, which is preferably a circular plate 14 enclosed by a cylindrical container 16, is capable of holding a plurality of cutting blades 10, so that more than one position is available for adequate washing. Each blade 10 is attached to the circular plate 14 by means of a fastener 18. As used in this context, the term "position" means a location on the circular plate 14 of the cutting blade holder 12. If the circular plate 14 of the cutting blade holder 12 has, for example, eight positions, one of the eight positions would be used for actuation of a cutting blade 10 for forming a slit in the stopper of a sample tube, while the other seven positions would be used for washing cutting blades 10.

In the wash operation, wash fluid will be dispensed, such as, for example, as a spray, onto the surface of the cutting blade 10. Wash operations are well-known to those having ordinary skill in the art of clinical analyzers. Subsequently, any residual wash fluid can be removed from the cutting blade 10 by means of a vacuum source. This operation can be repeated 2 to 4 times at each index position, and repeated up to seven (7) times, because seven (7) of the eight (8) index positions are available for washing operations.

The cutting blade holder 12, such as, for example, the circular plate 14 enclosed by a cylindrical container 16 for holding cutting blades 10, provides several advantages over a holder for a single cutting blade 10. Each cutting blade 10 must be washed to prevent contamination by carryover of the sample. The duration of this washing operation could exceed the period of time allocated for fulfilling throughput requirements of a closed tube sampling system. Accordingly, the cutting blade holder 12 would allow several cutting blades 10 to be used while one cutting blade 10 is undergoing washing to put it into condition for being reused.

Figure 6:
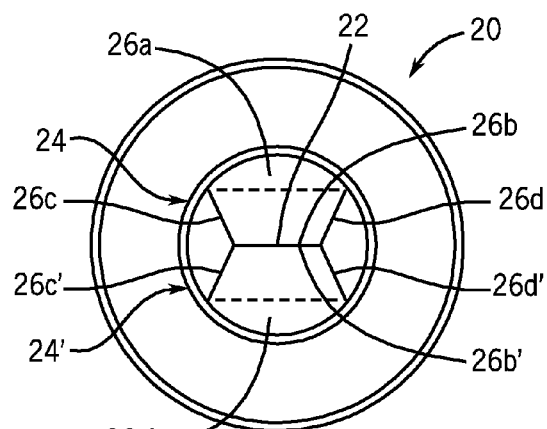
FIG. 6 is a top plan view of a stopper for a sample tube, the stopper having a slit formed by the cutting blade shown in FIGS. 1, 2, and 3.

FIG. 6 is a top plan view of a stopper 20 of a sample tube suitable for use herein. The stopper 20 of the sample tube is characterized by having a slit 22 formed by a cutting blade 10. The slit 22 is adjacent to a pair of flaps 24, 24' that can move toward the interior of a sample tube and away from the interior of the sample tube. As shown in FIG. 6, each flap 24, 24' has a trapezoidal shape. Each flap 24, 24' comprises (1) a longer side 26a, 26a' which is attached to the body of the stopper 20, (2) a shorter side 26b, 26b' which is parallel to the longer side 26a, 26a' but shorter than the longer side 26a, 26a' (3) a first side 26c, 26c' connecting one end of the longer side 26a, 26a' to one end of the shorter side 26b, 26b' and (4) a second side 26d, 26d' connecting the other end of the longer side 26a, 26a' to the other end of the shorter side 26b, 26b'. Preferably, the first side 26c, 26c' is not parallel to the second side 26d, 26d'. The shorter side 26b, 26b' runs through the center of the stopper 20. The longer sides 26a, 26a' are indicated by dashed lines, along which the flaps 24, 24', respectively, can flex. The cuts for forming the flaps 24, 24' can be made by the cutting blade 10 illustrated in FIGS. 1-3.

Figure 7:
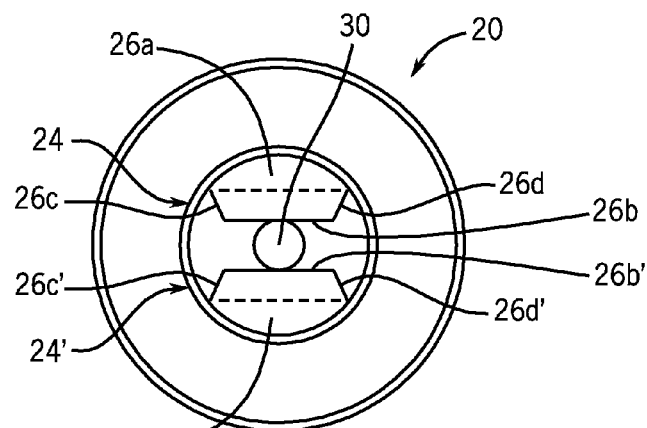
FIG. 7 is a top plan view of the stopper shown in FIG. 6, in which a device referred to herein as a sleeve/collar has been inserted into the slit.

Further, as a sample tube having a slit stopper 20 is transported to each immunoassay analyzer or clinical chemistry analyzer, a sleeve/collar 30 is inserted into the gap 32 between the flaps 24, 24' while the sample tube is being positioned for an aspirating step. See FIG. 7. This sleeve/collar 30 spreads the flaps 24, 24' to form a substantially rectangular-shaped opening between the spread flaps 24, 24'. The sleeve/collar 30 can be fabricated from a corrosion-resistant material, such as, for example, stainless steel, a polymeric material, or any other type of material that is suitable for manufacturing a sample aspirating probe. Another possible material for the sleeve/collar 30 is rigid PEEK (polyetheretherketone) tubing, a description of which is accessible by means of the Hypertext Transfer Protocol on the World Wide Web at the website coleparmer.com/catalog/product_index.asp?cls=6808, incorporated herein by reference. The sleeve/collar 30 has a bore, the dimensions of which bore must be large enough to receive a sample aspirating probe, but small enough so that the outside diameter of the sleeve/collar 30 can be made small enough so that the sleeve/collar 30 can traverse the slit 22 of the stopper 20 upon the application of a reasonable amount of force. The shape of the sleeve/collar 30 is not critical; however, it is preferred that the shape of the sleeve/collar 30 be cylindrical so that a sample aspirating probe can easily traverse the slit 22 of the stopper 20.

The sleeve/collar 30 has the functions of "spreading" the slit 22 in the stopper 20, while the sample aspirating probe is inserted into the sample tube through this sleeve/collar 30. The sleeve/collar 30 derives its name from its function of receiving the sample aspiration probe through the bore of the sleeve/collar. Accordingly, the sample aspirating probe does not contact the stopper 20, and sample carryover and washing requirements are reduced. As used herein, the plural form of the expression "sleeve/collar" is sleeve/collars. Subsequently, the sleeve/collar 30 can either be washed or disposed of.

As mentioned previously, the sample aspirating probe is inserted through the bore of the sleeve/collar 30 and aspirates a portion of the sample. In essence, the sample aspirating probe of the analyzer detects and processes the slit stopper 20 of the sample tube as it would a sample tube from which the closure has been removed; accordingly, no modification of the analyzer is required. Prior to inserting the sleeve/collar 30 into the slit 22, a detector for the stopper 20 of the sample tube will ensure that a slit stopper 20 is present. The sleeve/collar 30 is inserted into the slit 22 by means of a robotic device. If a slit stopper 20 is not present, then the detector indicates that the sample tube is open, and the sleeve/collar 30 is not used. After a sleeve/collar 30 is used, it can be washed to prevent contamination by carryover of the sample. In order to minimize reduction of throughput on account of washing of the sleeve/collar 30, a sleeve/collar holder substantially similar to the cutting blade holder 12 shown in FIGS. 4 and 5 can be used. The sleeve/collar holder is capable of holding a plurality of sleeve/collars 30, so that more than one position is available for adequate washing. As used in this context, the term "position" means a location on the circular plate of the sleeve/collar holder. If the circular plate of the sleeve/collar holder has, for example, eight positions, one of the eight positions would be used for actuation of a sleeve/collar 30 for forming a slit 22 in the stopper 20 of a sample tube, while the other seven positions would be used for washing sleeve/collars 30. As with the cutting blade holder 12, the sleeve/collar 30 holder will rotate (index) one position clockwise (or counter-clockwise, if desired), the used sleeve/collar 30 will be rotated into one of seven (7) possible wash positions, and a washed sleeve/collar 30 will be positioned in the aspiration location, as the next sample tube is moved into position for aspiration.

In the wash operation, wash fluid will be dispensed, such as, for example, as a spray, onto the interior surface and the exterior surface of the sleeve/collar 30. Wash operations are well-known to those having ordinary skill in the art of clinical analyzers. Subsequently, any residual wash fluid will be removed from the interior and exterior of the sleeve/collar 30 by means of a vacuum source. This operation can be repeated 2 to 4 times at each index position, and repeated up to seven (7) times, because seven (7) of the eight (8) index positions are available for washing operations. FIG. _ illustrates such a circular sleeve/collar holder.

The circular plate for holding sleeve/collars 30 provides several advantages over a holder for a single sleeve/collar 30. As with the cutting blades 10, each sleeve/collar 30 must be washed to prevent contamination by carryover of the sample. The duration of this washing operation could exceed the period of time allocated for fulfilling throughput requirements of the closed tube sampling system. Accordingly, the circular plate for holding sleeve/collars 30 would allow several sleeve/collars 30 to be used while one sleeve/collar 30 is undergoing washing to put it into condition for being reused.

In a typical cutting operation, while the sample tube is being firmly held in place, a cutting blade 10 (or set of cutting blades 10) will be lowered to the top of the stopper 20 of the sample tube. Subsequently, the blade will be plunged through the stopper 20, typically to a depth of about 1 inch. The stopper 20 will be held in place, so as to remain in the sample tube, as the cutting blade 10 is being retracted.

The circular plate 14 for holding cutting blades 10 will rotate (index) one position clockwise, the used cutting blade 10 will be rotated into one of seven (7) possible wash positions, and a cleaned cutting blade 10 will be positioned at the cutting location, as the next sample tube is being moved into this position.

For example, if the throughput requirement of a closed tube sampling system were 300 samples per hour, the time required for cutting a slit 22 in a stopper 20 of a sample tube would be twelve (12) seconds. Thus, twelve (12) seconds would be required for completing an operation for cutting a slit 22 in a stopper 20 and washing a cutting blade 10, in order for a cutting blade 10 to be available for cutting a slit 22 in the stopper 20 of the next sample tube. If detection of the stopper 20, centering of the sample tube, reading of the barcode of the sample tube, and cutting a slit 22 in the stopper 20 required nine (9) seconds, then washing and drying of the cutting blades 10 for cutting a slit 22 in the stopper 20 would be required to be completed in three (3) seconds (12 seconds minus 9 seconds). Because current wash times for the sample aspirating probe of an "ARCHITECT" immunoassay analyzer range from seven (7) to ten (10) seconds, allocation of wash time of three (3) seconds for the cutting blade 10 for cutting a slit 22 in the stopper 20 would not be sufficient. Accordingly, a plurality of index positions provided by the circular plate 14 for holding cutting blades 10 would allow sufficient time for washing the cutting blades 10 that are not being used.

Wear data derived from hematology analyzers suggest that vent needles for a closed tube sampling system need to be replaced after approximately 5000 piercings of stoppers. This degree of wear results from the high level of friction between the vent needle, which is made of metal, and the stopper of the sample tube, which is made of rubber. Assuming this replacement rate for a mechanism for cutting slits in stoppers, a significant level of maintenance and downtime of the analyzer would be required on a daily basis in a high volume laboratory. A circular plate 14 enclosed by a cylindrical container 16 for holding cutting blades 10, for example, eight cutting blades 10 for cutting stoppers, would improve the replacement rate to approximately 40,000 cuttings of stoppers. The size of the circular plate 14 for holding cutting blades 10 can be selected to meet the maintenance and sample volume requirements of a particular laboratory.

Cutting blades 10 for stoppers 20 are designed to be extremely sharp and present a significant safety hazard to the operator or service personnel handling them. A circular plate 14 enclosed by a cylindrical container 16 for holding cutting blades 10 for cutting slits 22 in stoppers 20 could eliminate these hazards, provide containment of cutting blades 10 for cutting slits 22 in stoppers 20, and allow operators to perform maintenance of cutting blades 10 for cutting slits 22 in stoppers 20, thereby replacing trained service personnel, with the result that a significant cost saving and convenience to the laboratory can be achieved.

It is important to note the distinction between sample tubes for hematology tests and sample tubes for immunoassays and clinical chemistry assays. As mentioned previously, when immunoassay analyzers and clinical chemistry analyzers are integrated with hematology analyzers, sample tubes must be loaded with stoppers in place (closed-tube system), because the hematology analyzer mixes the entire sample of blood by inverting the tube several times, thereby ensuring uniform distribution of blood cells. Subsequent to aspirating a sample for a hematology analysis, aliquots can be drawn from the closed tube and subsequently routed to a centrifuge and then to appropriate immunoassay analyzers and clinical chemistry analyzers for analysis. If immunoassay analyzers and clinical chemistry analyzers are not integrated with hematology analyzers, the sample tubes can be "open" or "closed". If sample tubes are "open" (stopper is removed), then all aliquots are withdrawn in the same manner as with the current "ARCHITECT" analyzers. If sample tubes are "closed" (stopper is in place), then either the stopper is cut at a cutting station and the sample tubes subsequently routed to analyzers for withdrawing of samples, or aliquots are withdrawn from the closed tube and subsequently routed to immunoassay analyzers and clinical chemistry analyzers for analysis.

As described in U.S. Pat. No. 7,678,331 B2, incorporated herein by reference, a device for elevating a sample tube in a sample tube carrier can be used to enable the stopper of the sample tube to be punctured by a piercing element in a piercing assembly. After the stopper of the sample tube is punctured, a probe for aspirating the sample from the sample tube can collect the sample in the receptacle of the sample tube through a bore in the piercing element. A vent needle is used to pierce stoppers of sample tubes prior to aspirating a portion of a sample. While the sample tube is held firmly, a vent needle with a specially designed tip is thrust through the stopper, and will expose the interior of the sample tube to the surrounding environment, whereby the pressure within the sample tube and the atmospheric pressure are equalized. Subsequently, a probe for aspirating a portion of the sample from the sample tube is inserted through the bore of the vent needle. After the sample is aspirated, the stopper will be held in place, so as to remain in the sample tube while the vent needle is being retracted. Additional information relating to puncturing a stopper of a sample tube can be found at column 15, line 31 through column 16, line 39 and at column 18, line 25 through column 19, line 23 of U.S. Pat. No. 7,678,331B2, previously incorporated herein by reference, and in FIGS. 22, 26, 27A, 27B, 27C, 27D, 28, 29, and 30 of U.S. Pat. No. 7,678,331 B2, previously incorporated herein by reference.

As with a circular plate 14 for holding cutting blades 10, the vent needle holder is rotated (indexed) one position clockwise, the used vent needle is rotated into one of seven (7) possible wash positions, and a washed vent needle is positioned in the piercing location, as the next sample tube is being moved into the appropriate position.

Wear data derived from hematology analyzers suggest that vent needles for a closed tube sampling system need to be replaced after approximately 5000 piercings of stoppers. This degree of wear results from the high level of friction between the vent needle, which is made of metal, and the stopper of the sample needle, which is made of rubber. Assuming this replacement rate for vent needles for piercing stoppers, a significant level of maintenance and downtime of the analyzer would be required on a daily basis in a high volume laboratory. A circular plate for holding vent needles, for example, eight vent needles, would improve the replacement rate to approximately 40,000 piercings of stoppers. The size of the circular plate for holding vent needles can be selected to meet the maintenance and sample volume requirements of a particular laboratory.

Vent needles for stoppers are designed to be extremely sharp and present a significant safety hazard to the operator or service personnel handling them. A circular plate enclosed by a cylindrical container for holding vent needles for piercing stoppers could eliminate these hazards, provide containment of vent needles for piercing stoppers, and allow operators to perform maintenance of vent needles for piercing stoppers, thereby replacing trained service personnel, with the result that a significant cost saving and convenience to the laboratory can be achieved.

Figure 8C:
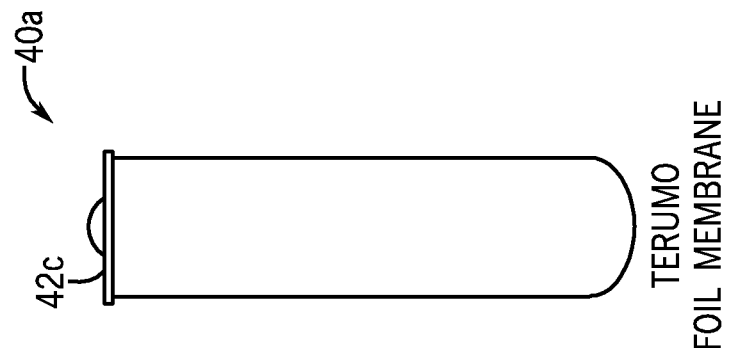
FIGS. 8A, 8B, and 8C are side views in elevation of sample tubes suitable for use in the sampling systems described herein.
Figure 8B:
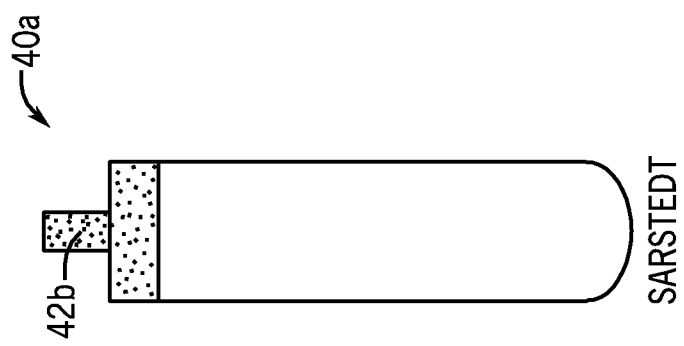
Figure 8A:
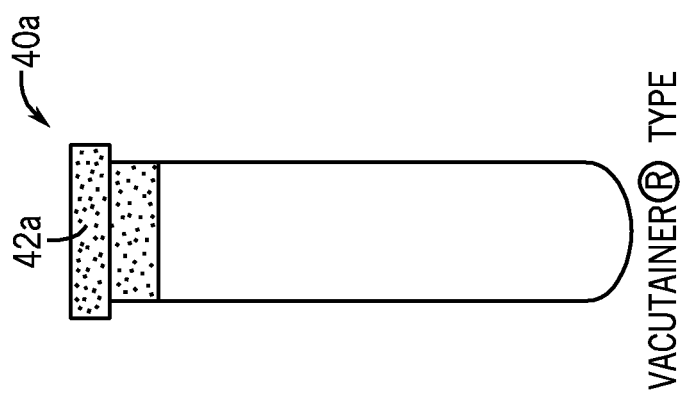

FIGS. 8A, 8B, and 8C illustrate several types of sample tubes 40a, 40b, and 40c, respectively, suitable for use with the systems described herein. Each of the sample tubes 40a, 40b, and 40c has a different type of stopper 42a, 42b, and 42c, respectively. However, other types of sample tubes can also be used with the systems described herein. This apparatus and method described herein are designed to function with sample tubes that are equivalent to or similar to "VACUTAINER" sample tubes that have pierceable stoppers.

Sampling Systems

FIG. 9 illustrates a configuration of a closed tube sampling system 100 capable of employing at least one immunoassay processing module 102 comprising at least one immunoassay analyzer, at least one clinical chemistry processing module 104 comprising at least one clinical chemistry analyzer, at least one hematology module 106 comprising at least one hematology analyzer, at least one module 108 for cutting slits in stoppers of sample tubes, and at least one module 110 for functions specified by a given laboratory, such as, for example, centrifugation, other means of separating components from samples. The at least one immunoassay processing module 102 includes a Local Sample Handler 102a and a wash station 102b. The at least one clinical chemistry processing module 104 includes a Local Sample Handler 104a and a wash station 104b. The at least one hematology module 106 includes a Local Sample Handler 106a and a wash station 106b. Although FIG. 9 illustrates three different types of clinical analyzers, it should be understood that not every configuration of sampling systems requires that all three types of clinical analyzers be used in every system. For example, each type of analyzer can be employed by itself, or any two different types of analyzers can be employed together, or all three types of analyzers can be employed together. In addition, the system shown in FIG. 9 reserves space for auxiliary components, such as, for example, an unloader 112 for sample tubes, an aliquot tube loader 114, various positions 116a, 116b, etc. for sample tubes in sample tube carriers, and a track or belt 118 for transferring sample tubes to the various processing modules and areas for storing samples.

Sample tubes that have stoppers and that have undergone centrifugation are introduced into the closed tube sampling system 100 by means of sample tube carriers 110. A robotic sample handler (not shown) prioritizes carriers of STAT samples ahead of carriers for routine samples.

Figure 10:
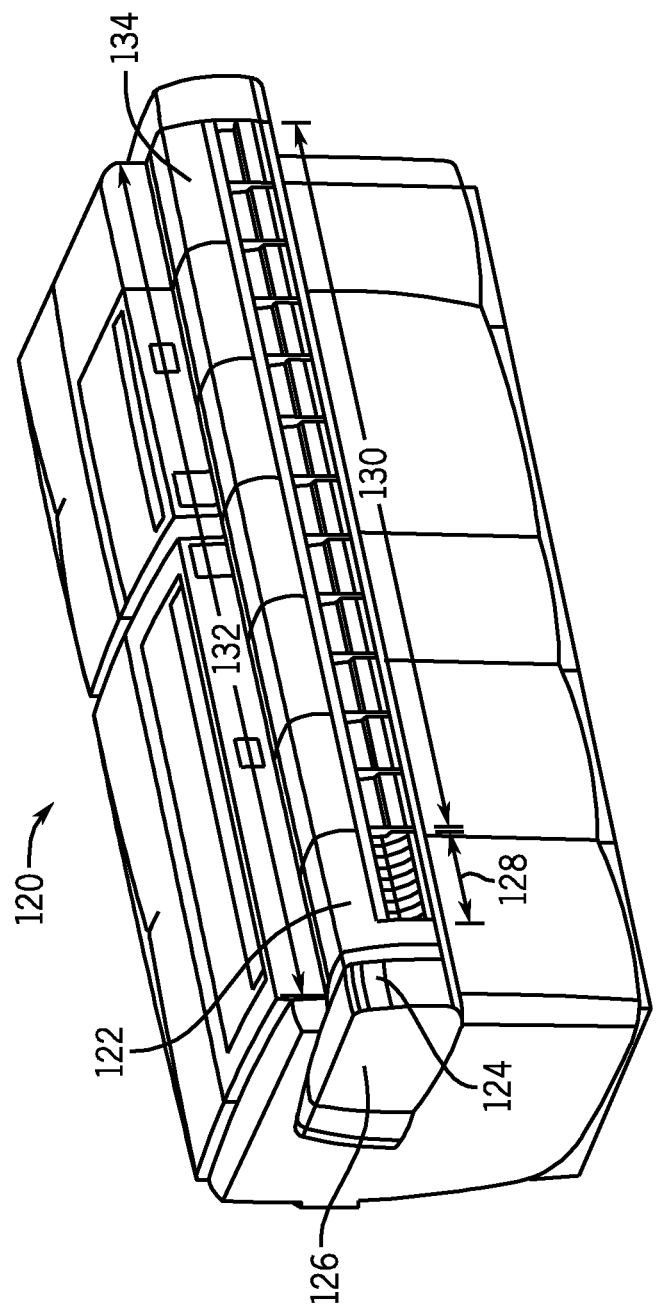
FIG. 10 is an isometric view of a clinical analyzer suitable for use with the system illustrated in FIG. 9.

Referring now to FIG. 10, a robotic sample handler 120 is a transport system used for loading calibrators, controls, patient samples, if needed, and reagents and presenting them to the processing module(s) of a system including at least one automated clinical analyzer. The robotic sample handler 120 allows random and continuous access for carrying out loading and unloading functions, and positioning of samples for automatic retesting. Samples can be positioned in two types of bays for either routine or priority processing. Referring again to FIG. 10, the robotic sample handler 120 comprises a cover 122 for providing access to components of the robotic sample handler 120, a keypad 124 for providing a local user interface for controlling the robotic sample handler 120, a barcode reader 126 for reading the identification indicia of samples and sample tube carriers, a priority bay 128 for positioning samples for priority processing, a routine bay 130 for positioning samples for routine processing, a carrier positioner 132 for positioning carriers for sample aspirating probes, a carrier transport 134 for transferring sample tube carriers from the bays 128, 130 to the carrier positioner 132 and returning sample tube carriers from the carrier positioner 132 to the bays 128 and 130.

The barcode reader 126 for sample tube carriers reads barcode labels on sample tubes and barcode labels on sample tube carriers. A barcode reader for reagent carriers (not shown) reads the two-dimensional barcode labels on reagent bottles. The carrier transport for sample tube carriers transfers sample tube carriers from loading bays 128 and 130 to the area for aspirating samples and returns the sample tube carriers to the loading bays 128 and 130. The carrier transport for reagent carriers (not shown) transfers reagent carriers from reagent loading areas (not shown) to the reagent carousel (not shown) and returns the reagent carriers to the reagent loading areas.

Additional details relating to the robotic sample handler previously described can be found in U.S. Pat. No. 7,458,483, incorporated herein by reference.

In the closed tube sampling system, a barcode reader reads the barcode on a sample tube. The presence of a stopper 20, if any, on the sample tube is detected, and, if a stopper 20 is present, a cutting blade 10 cuts a slit 22 in the stopper 20 on the sample tube (if required). Cutting a slit is not always required. Under certain circumstances, a stopper may have been removed before the sample tube is loaded onto the system. Such circumstances include, but are not limited to, testing on a different system that may have required the stopper 20 to be removed.

The sample tube that is closed by the slit stopper 20 is routed for testing, held for retesting, if required, and then made available for unloading if and when results indicate that no retesting required. When a sample tube having a slit stopper 20 is transported to an immunoassay analyzer 102 or to a clinical chemistry analyzer 104, and a stopper 20 is detected on the sample tube, a sleeve/collar 30 (not shown in FIGS. 9 and 10) is inserted into the slit 22, while the sample tube is positioned for a step for aspirating samples. After the sleeve/collar 30 is used in the step for aspirating samples, the sleeve/collar 30 is washed to prevent contamination of the sample or the sample aspirating probe or both by carryover of the sample. In essence, the sample aspirating probe of the analyzer treats the sample tube having a slit stopper 20 as an "open" sample tube, with the result that no modification of a commercially available analyzer that uses open tubes is required.

An "Open Cannula" closed tube sampling design, which is incorporated into the "CELL-DYN" Sapphire™ hematology analyzer (commercially available from Abbott Laboratories), can be incorporated into the systems described herein. See, for example, column 15, line 31 through column 16, line 39 and at column 18, line 25 through column 19, line 23 of U.S. Pat. No. 7,678,331 B2, previously incorporated herein by reference, and in FIGS. 22, 26, 27A, 27B, 27C, 27D, 28, 29, and 30 of U.S. Pat. No. 7,678,331 B2, previously incorporated herein by reference. In this design, the stopper on the sample tube is not slit. Instead, the barcode reader of the closed tube sampling module reads the barcode of the sample tube, detects the presence of a stopper on the sample tube, and penetrates the stopper, if required, with a custom-designed vent needle. The vent needle has an elongated bore for receiving a sample aspirating probe. The types of sample tubes that can be used are not as limited as those suitable for the embodiment shown in FIGS. 9 and 10. While the vent needle is embedded in the stopper, a sample aspirating probe, which is referred to as an "open cannula" is inserted into the bore of the vent needle, whereby it traverses the stopper, thereby allowing aspiration of the sample. Cutting slits 22 in stoppers 20 cannot be carried out for all types of sample tubes, because the cutting blade 10 may have a width greater than the diameter of the elastomeric portion of the stopper 20. The "Open Cannula" design is compatible with most types of commercially available sample tubes, including those using stoppers having elastomeric portions having small diameters.

A circular plate substantially similar to that shown in FIGS. 4 and 5 can be used for holding vent needles during an operation for washing vent needles. The benefits described for the circular plate 14 for holding cutting blades 10 and sleeve/collars 30 are also applicable to a circular plate for holding vent needles; accordingly, a circular plate for holding vent needles provides the following advantages over a holder for washing a single vent needle: (a) decrease of throughput is reduced and increased time for washing is allowed; (b) life of consumable items is increased (40,000 piercings rather than 5,000), and (c) safety of operators is enhanced by containing sharp items.

According to another embodiment of a closed tube sampling system, the components include at least one immunoassay analyzer, at least one clinical chemistry analyzer, and at least one sample tube aspirating module for aspirating samples from sample tubes. The operator loads sample tubes having stoppers by means of sample tube carriers, and the robotic sample handler prioritizes sample tube carriers holding STAT samples ahead of sample tube carriers holding routine samples. The sample tubes have not undergone centrifugation or any other separation technique. The barcode reader of the closed tube sampling module reads the barcode on the sample tube, detects presence of a stopper, if any, on the sample tube, and, if a stopper is present, a piercing element pierces the stopper on the sample tube (if required) or a cutting blade cuts a slit in the stopper (if required). In this embodiment, the sample tube aspirating module transfers a specified volume of the sample to an aliquot tube. The sample tube carrier can then be unloaded. The sample in the aliquot tube is routed for testing, held for retesting, and then disposed if and when results indicate that no retesting is required. An operator can load samples having small volumes by means of individual sample cups. Interaction with the system by the operator is required for positive identification of a sample at a location for STAT samples. Because sample cups typically do not have barcodes, the operator is required to enter certain data to ensure that the sample being drawn from the sample tube is the sample for which tests have been ordered (i.e., positive identification of a sample). Special loading areas are used for STAT samples, in order to bypass the queue typically associated with routine sample handling.

Calibrations for assays are performed at the analyzers by means of local sample handlers. A local sample handler is a device, e.g., a small carousel, for loading and unloading samples at each clinical analyzer. A local sample handler is typically used for STAT samples, controls, calibrators. An advantage of this embodiment is that the aliquot tubes for the samples are "open" sample tubes, with the result that no modification of a commercially available analyzer is required.

A blood separation technique can be selected and used to integrate hematology analyzer(s), immunoassay analyzer(s), and clinical chemistry analyzer(s), whereby one sample collection tube can be used for all three areas of testing, thereby providing the laboratory with a significant advantages and reducing the labor required to sort samples, centrifuge samples, and distribute samples to the appropriate analyzer(s).

According to one separation technique for separating blood cells from serum or plasma, magnetically attractable particles are coated with an agglutinating reagent, such as, for example, a lectin, which is a sugar binding protein that binds to walls of cells. When these particles are added to a sample of whole blood, these particles immediately (i.e., within about two (2) minutes) bind with cells, and, subsequently, these cells can be separated from the plasma by means of magnetic attraction. This separation technique has been shown to be effective, i.e., the separation technique removes 99.99% of red blood cells and removes 92.14% of white blood cells.

According to another separation technique for separating blood cells from serum or plasma, a standing ultrasonic wave (1.5-2.0 MHz, 12 volts peak-to-peak) can be used to separate the components within a sample of whole blood. Ultrasonic energy can be applied to a sample of whole blood in an aliquot tube. Cells are separated from plasma by density between nodes and peaks of ultrasonic waves, i.e., red blood cells, which have the highest density, are separated from plasma at the node of a standing wave, and lipids, which have the lowest density are separated at the peaks of a standing wave. Cells having varying densities would be distributed between the nodes and the peaks of a standing wave. This blood separation technique or an alternative blood separation technique can also be used to integrate hematology analyzer(s), immunoassay analyzer(s), and clinical chemistry analyzer(s), whereby one sample collection tube can be used for all three areas of testing.

Until the aforementioned magnetically attractable particle technique and standing ultrasonic wave technique are perfected, centrifugation will typically be used to treat biological samples prior to carrying out immunoassays and clinical chemistry tests.

Continuous Access Centrifuge

Figure 11:
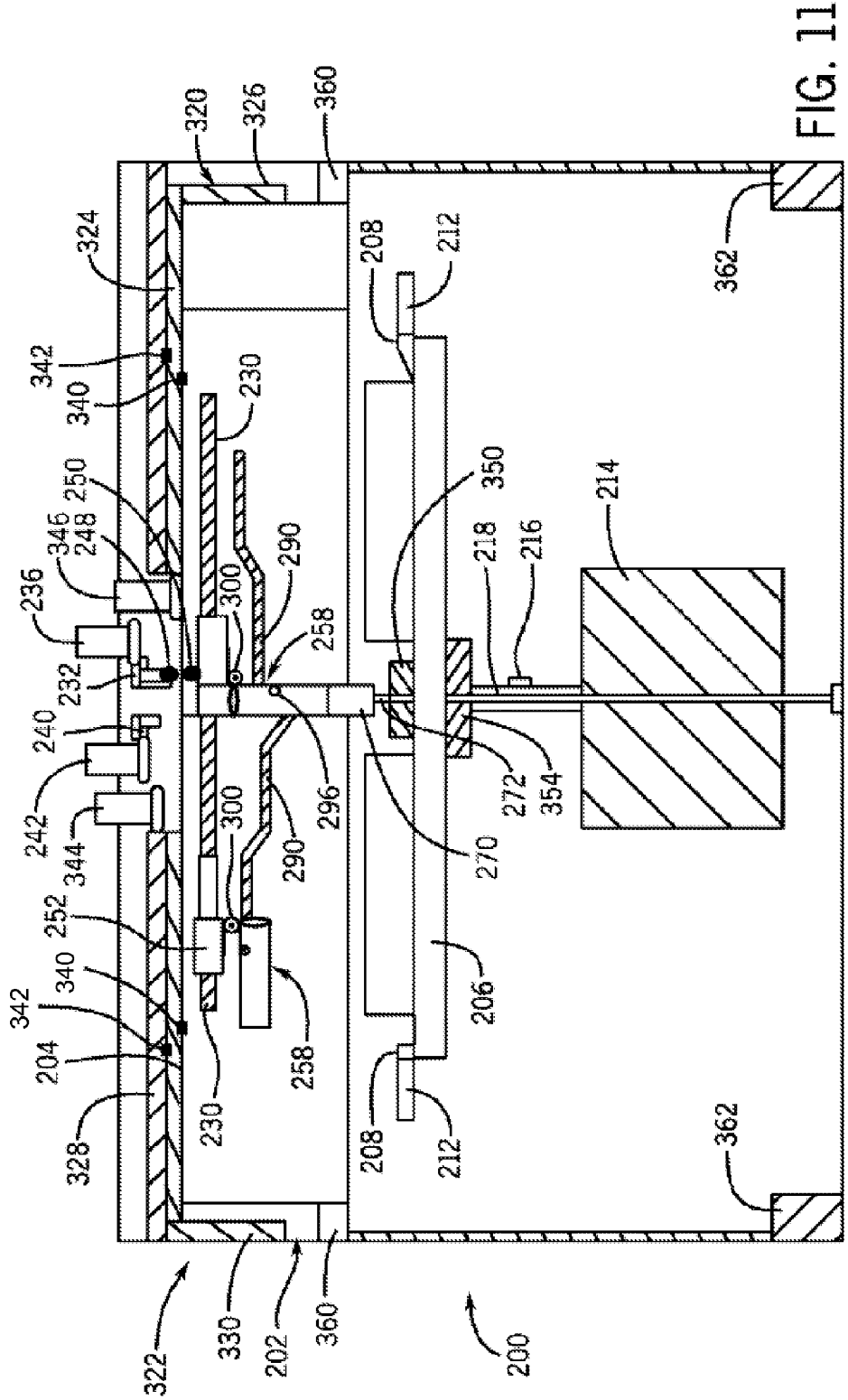
FIG. 11 is a cross-sectional view of an embodiment of a centrifuge described herein. In this embodiment, an exterior balancing cap and an interior balancing cap are employed to cancel imbalance vectors generated by the centrifuge.
Figure 12:
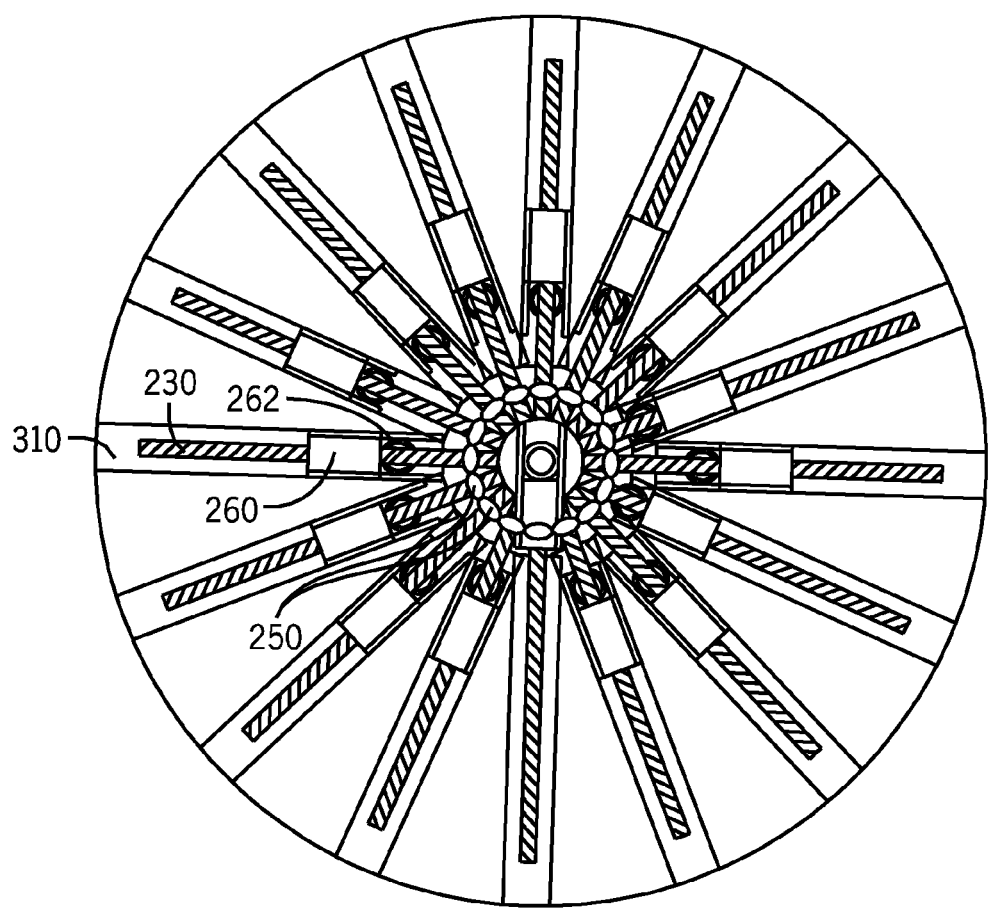
FIG. 12 is a plan view illustrating the upper portion of the carousel of the centrifuge described herein.

FIGS. 11-21 illustrate a system for treating a biological sample by means of centrifugation. In FIGS. 11-21, unless otherwise indicated, only one of each plurality of identical components will receive a reference numeral. For example, if twenty-five lead screws are shown, only one of these twenty-five lead screws will receive a reference numeral. Referring now to FIG. 11, a centrifuge 200 comprises a carousel 202 having an upper portion 204 and a lower portion 206. FIG. 12 illustrates that the upper portion 204 of the carousel has a plurality of positions for sample tubes for a centrifugation operation. Assuming a centrifugation step has a duration of five minutes, twenty-five (25) positions would be required to prepare 300 samples per hour.

Figure 13:
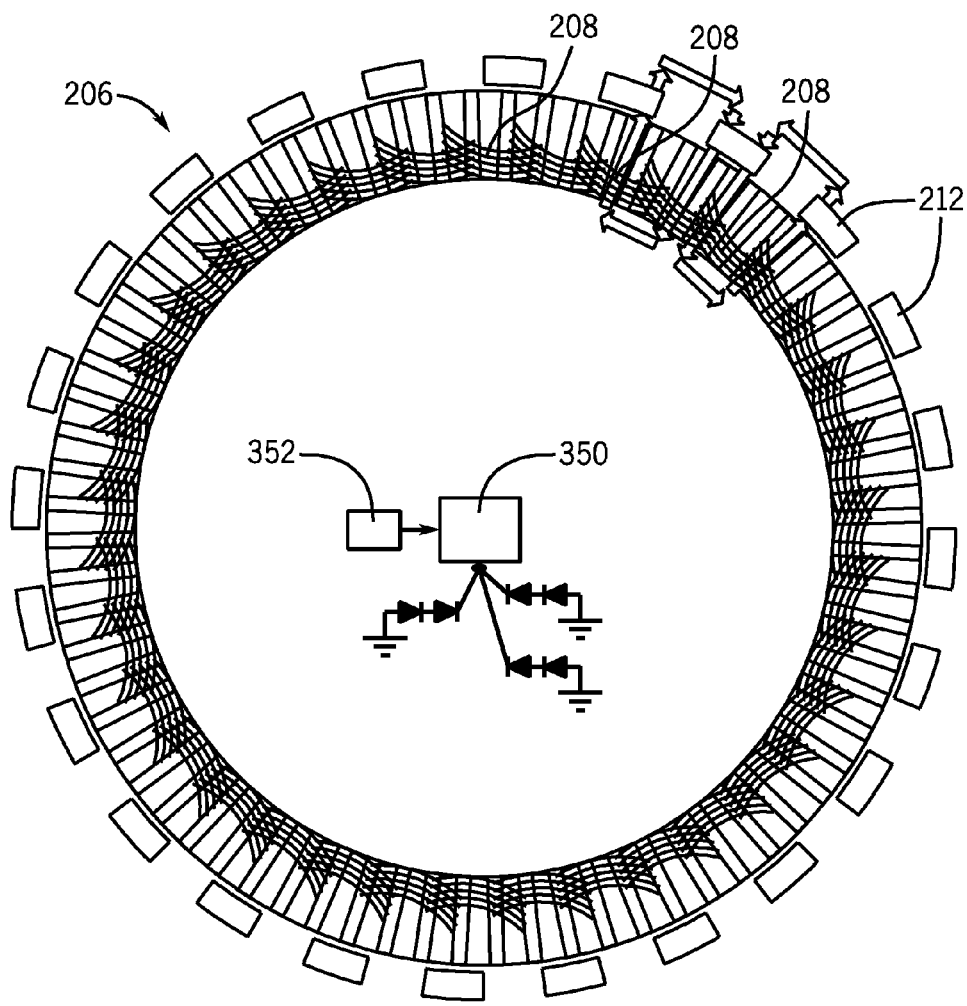
FIG. 13 is a plan view illustrating the lower portion of the carousel of the centrifuge described herein.

FIG. 13 illustrates a plurality of rotor coils 208 mounted on the lower portion 206 of the carousel 202. Thirty-six (36) rotor coils are shown in FIG. 13. FIG. 13 illustrates a plurality of field coils 212 mounted around the periphery of the lower portion 206 of the carousel 202. Twenty-four (24) field coils are shown in FIG. 13. A rotor coil is a device in which electrical energy is induced by motion through a magnetic field. The rotor coils are located on the rotating part of the electric machine (called a rotor). A field coil is a device which provides the magnetic field within which the rotor moves. The field coils 212 (or permanent magnets) are located on a stationary part of the electric machine (called a stator). The aforementioned system of rotor coils 208 and field coils 212 is analogous to an alternator, which is an engine that converts mechanical energy into alternating current (AC) electrical energy by electromagnetic induction. Also shown in FIG. 11 are a motor 214 for rotating a shaft 216 for rotating the carousel 202, and a bore 218 in the shaft 216, for accommodating auxiliary components that are used to enhance the performance of the centrifuge 200.

In the embodiment shown in FIG. 13, the field, which is stationary, can be adjusted through the use of an electromagnet. Alternatively, in the embodiment shown in FIG. 13, the field can be fixed through the use of permanent magnets. Either alternative is suitable for the centrifuges described herein.

A plurality of loops can be wound around a laminated sintered iron core for the centrifuge rotor. The loops are typically made of sixteen or fourteen gauge wire, and each coil typically comprises 200 loops. A stator magnet suitable for use herein can have dimensions of ½ inch×½ inch×½ inch, with N42 or N52 rating. See, for example, the subject matter accessible by means of the Hypertext Transfer Protocol on the World Wide Web at the website kjkmagnetics.com/proddetail.asp?prod=BX8X8×8%2DN52, incorporated herein by reference. Descriptions of direct-current machines, alternating current machines. converters, and various types of machinery that can be used to run the carousel 202 of the centrifuge 200 can be found in *THE WAY THINGS WORK*, Volume 2, Simon and Schuster (New York: 1971), pages 506-517, incorporated herein by reference. One of ordinary skill in the art would be able to use these descriptions to develop a carousel 202 suitable for the centrifuge 200 described herein.

Referring now to FIG. 12, attached to the upper portion 204 of the carousel 202 is a plurality of lead screws 230, each lead screw 230 defining a path for a sample tube. Referring again to FIG. 11, the lead screws 230 are driven by an arrangement comprising a transmission case 232, a first circular bearing (not shown), a stepper motor 236 for driving the transmission case 232, a second circular bearing (not shown) for supporting a ring gear 240, a stepper motor 242 for driving the ring gear 240, a post (not shown) and a bearing (not shown) for supporting a drive gear 248, and a plurality of lead screw gears 250. Each lead screw gear 250 is associated with a specific lead screw 230. The post (not shown) can be a cast feature of the transmission case 232, or a screw, rivet, or other fastener that extends radially from the lowermost portion of the transmission case 232. The post is just below the ring gear 240. The bearing associated with the post is internal to the drive gear 248, and surrounds the post in such a manner that the teeth of the drive gear 248 engage the teeth on the bottom of the ring gear 240 and the teeth on a selected lead screw gear 250 simultaneously.

The transmission case 232 is attached to the carousel 202 by means of the first circular bearing (not shown). Gear teeth are machined on the top of the transmission case 232, at the periphery thereof. The transmission case 232 is rotated by the stepper motor 236. Attached to the transmission case 232 is the second circular bearing (not shown), which supports the ring gear 240. Gear teeth are machined on the periphery and on the bottom of the ring gear 240. The ring gear 240 is driven by the stepper motor 242. The transmission case 232 and the ring gear 240 can rotate independently of one another. Attached to the transmission case 232 are the post (not shown) and the bearing (not shown), which support the drive gear 248. Gear teeth are machined on the drive gear 248, and these gear teeth are engaged to the bottom of the ring gear 240 and to the top of one of the lead screw gears 250, when the particular lead screw gear 250 is selected. The components not shown are well-known to those having ordinary skill in the art, and the transmission mechanism described herein can readily be constructed by one having ordinary skill in the art by means of commercially available components.

Figure 14:
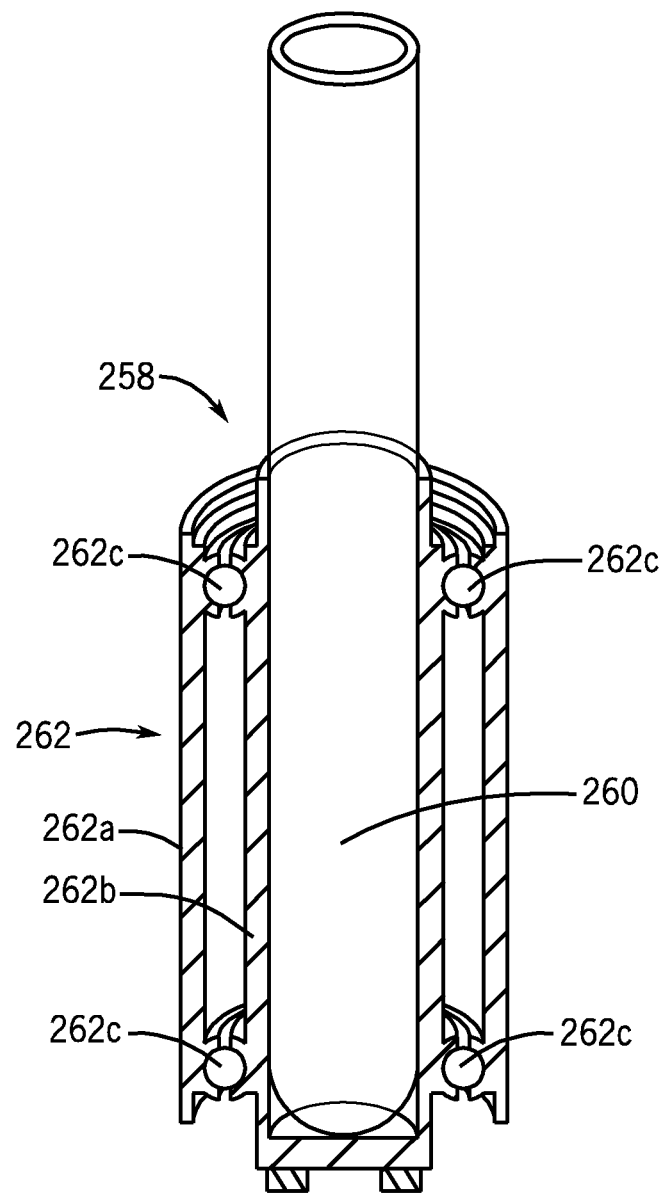
FIG. 14 is a perspective view of a sample tube-holding assembly, showing a sample tube holder and a bearing.
Figure 15A:
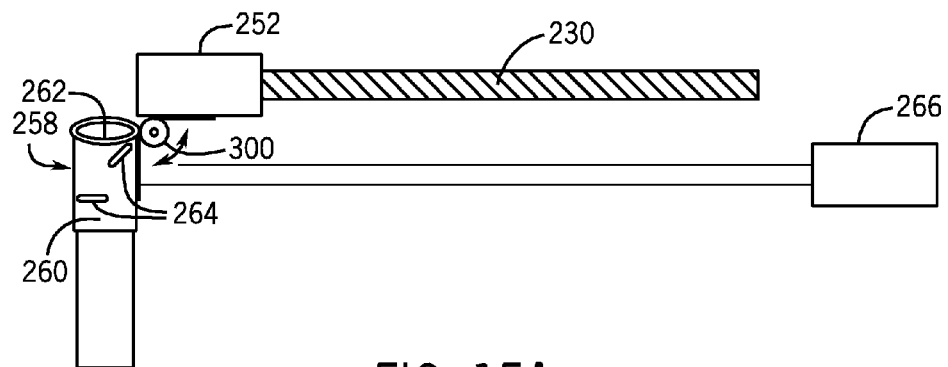
FIGS. 15A, 15B, 15C, and 15D are side views illustrating an emitter-detector and a reflector indicating the angle of inclination of a sample tube during operation of the centrifuge described herein.
Figure 15B:
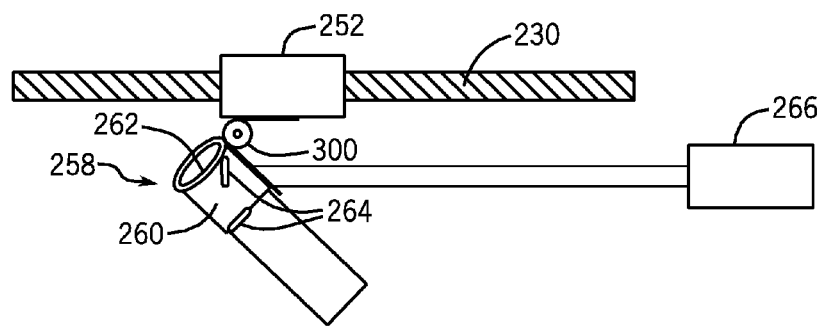
Figure 15C:
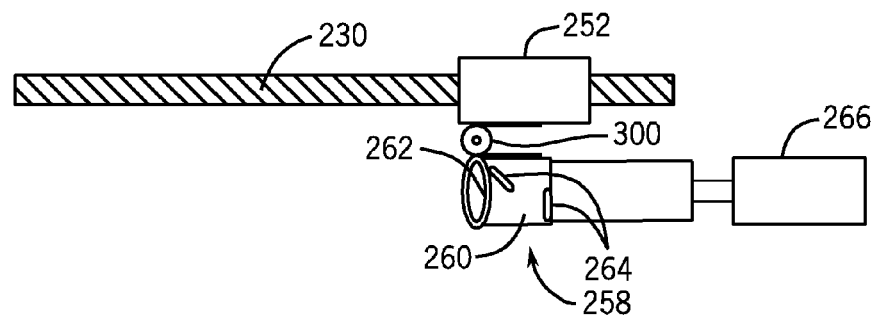
Figure 15D:
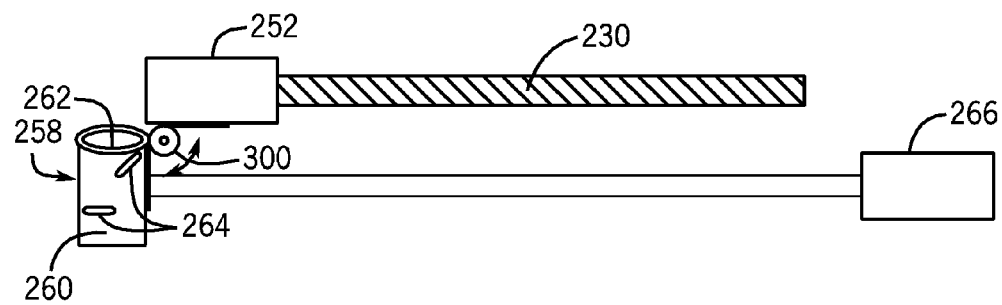

Mounted upon each lead screw 230 is a lead screw nut 252 that is capable of traversing the length of the lead screw 230 when the lead screw 230 is actuated. Attached to each lead screw nut 252 by means of a torsion spring 256 is an assembly 258 for holding sample tubes, hereinafter referred to as a sample tube-holding assembly 258. The sample tube-holding assembly 258 comprises a sample tube holder 260 and a bearing 262. As shown in FIG. 14, the bearing 262 has an outer race 262a and an inner race 262b. The outer race 262a and the inner race 262b are separated by ball bearings 262c. Each sample tube holder 260 is journaled in a bearing 262, whereby a brake at the load/unload position can prevent the sample tube from rotating while the carousel 202 continues to rotate, even at full speed), thereby enabling a more reliable pick and place operation by the robotics associated with the centrifuge 200.

In operation, a lead screw gear 250 is "selected" by rotating the transmission case 232 by means of the stepper motor 236. The lead screw gear 250 thus selected drives the specific lead screw 230 with which it is associated. This movement causes the teeth of the drive gear 248 to engage the teeth of the selected lead screw gear 250. Because the teeth of the drive gear 248 are always engaged with the teeth of the ring gear 240, rotating the ring gear 240 by means of the ring gear stepper motor 242 will cause the drive gear 248 and the selected lead screw gear 250 to rotate. Rotation of the selected lead screw gear 250 causes the selected lead screw 230 to rotate, thereby moving the lead screw nut 252 mounted on the selected lead screw 230.

Referring now to FIGS. 15A, 15B, 15C, and 15D, each sample tube-holding assembly 258 includes a reflector(s) 264 for reflecting a signal emitted by an emitter-detector 266. The emitter-detector 266 can be of the type that uses a light emitting diode, alternatively referred to herein as "LED emitter-detector." An emitter-detector 266 is positioned in such a manner so as to be able to detect the reflector on a sample tube holder 260. The position of the sample tube-holding assembly 258 can be verified by means of the reflector(s) 264 and the emitter-detector 266. The emitter-detector 266 emits a beam of light. The beam of light emitted from the emitter-detector 266 is reflected from the reflector 264 when the sample tube holder 260 is parallel to the axis of the carousel 202. The beam of light emitted from the emitter-detector 266 is not reflected from the reflector 264 when the sample-tube holding assembly 258 is tilted to such an extent that the reflector 264 is not struck by the beam of light emitted from the emitter-detector 266.

The reflector 264 positioned between a sample tube holder 260 and an emitter/detector 266 can be used to verify the various inclinations from the vertical position of the sample tube holders 260. Reflector(s) are positioned on the sample tube holder 260 such that the 45° position tab provides a reflective surface for the 45° LED emitter-detector 266 only when the sample tube holder 260 is inclined at an angle of 45°. Further, the 90° reflector(s) 264 provides a reflective surface for the 90° LED emitter-detector 266 only when the sample tube holder 260 is in the 90° position. Thus, the angle of inclination of a sample tube can be verified when the sample tube holder 260 is inclined at a specified angle. Emitter-detectors 266 suitable for use herein are commercially available and are further described by means of the Hypertext Transfer Protocol on the World Wide Web at the website vishay.com/docs/83795/tcnd5000.pdf, incorporated herein by reference.

In the centrifuge 200 described herein, the lead screws 230 have fine threads and the threads have a sufficiently small helix angle such that a lower quantity of torque is required to move and maintain the position of a lead screw nut 252, as compared with substantially similar lead screws having coarse threads. For a lead screw nut 252 to move a given distance, additional rotations are required for a lead screw 230 having fine threads, as compared with a substantially similar lead screw having coarse threads; however, it is not critical that traversal of the length of the lead screw 230 by a lead screw nut 252 be effected in a certain period of time. Moreover, the use of lead screws 230 having fine threads actually provides more precise positional adjustment of the lead screw nut 252. Furthermore, lead screws 230 having fine threads are stronger than lead screws having coarse threads, given the same hardness of the material from which the lead screw is made. This increase in strength is found in both the tension mode and the shear mode, on account of the slightly larger tensile stress area and the slightly larger minor diameter of lead screws having fine threads.

A magnetic brake 270, shown in FIG. 11, is designed to be in register with the bottom of each sample tube holder 260 when the sample tube holder 260 is positioned at the center of the carousel 202. Magnetic brakes 270 suitable for use herein are further described by means of the Hypertext Transfer Protocol on the World Wide Web at the website kjmagnetics.com/proddetail.asp?prod=D44%2DN52, incorporated herein by reference. A magnet is attached to the lowermost portion of each sample tube holder 260. A vertically-oriented rod 272 projecting through an opening in the lower portion 206 of the carousel 202 of the centrifuge 200 supports the stationary magnetic brake 270. The magnetic brake 270 can use a permanent magnet or an electromagnet. In addition, to accommodate the vertically-oriented rod 272, the shaft 216 of the motor 214 has a bore 218 formed therethrough.

Figure 16A:
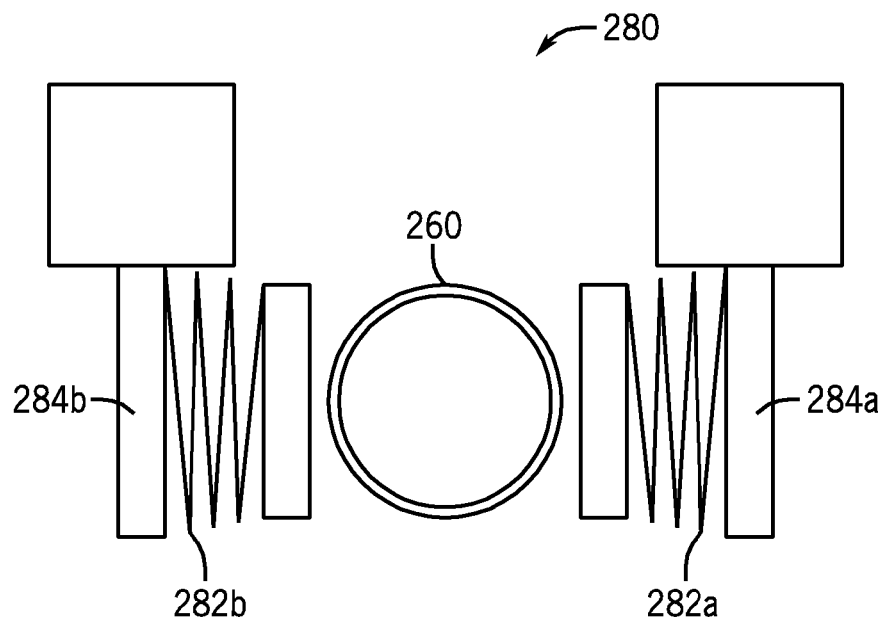
FIG. 16A is a plan view showing a clamp brake about to contact a sample tube holder.
Figure 16B:
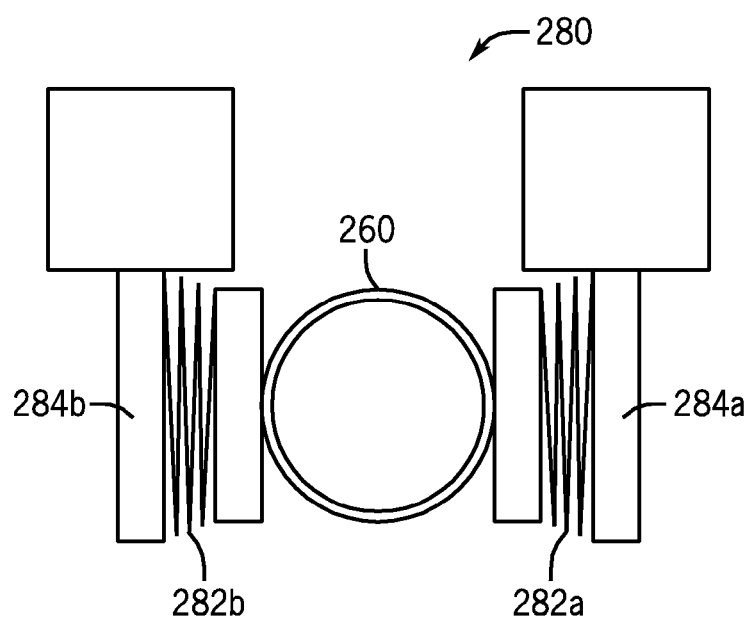
FIG. 16B is a plan view of the clamp brake of FIG. 16A, wherein the clamp brake is contacting the sample tube holder.
Figure 17A:
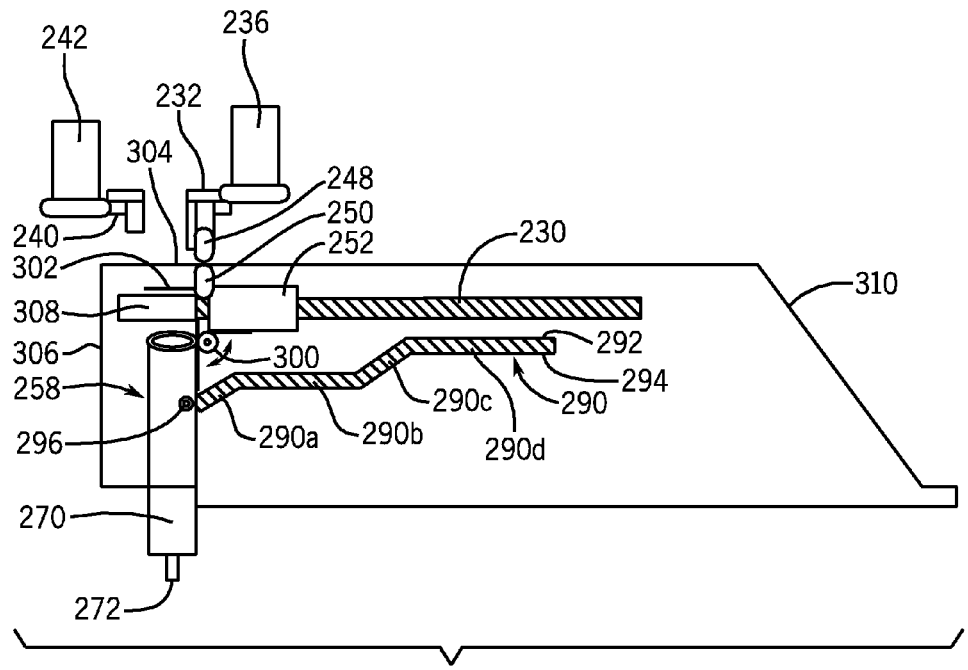
FIG. 17A is a side view illustrating a sample tube in the load/unload position of the centrifuge.
Figure 17B:
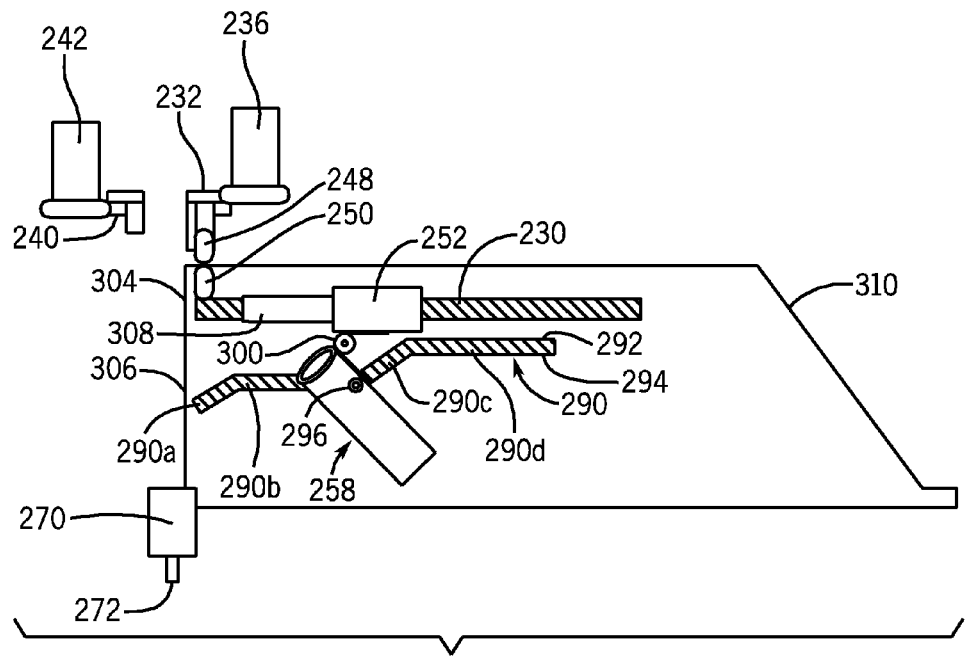
FIG. 17B is a side view illustrating the sample tube of FIG. 17A tilted at an angle of 45° in the centrifuge, in which the sample tube is part way between the load/unload position of the centrifuge and the periphery of the centrifuge.
Figure 17C:
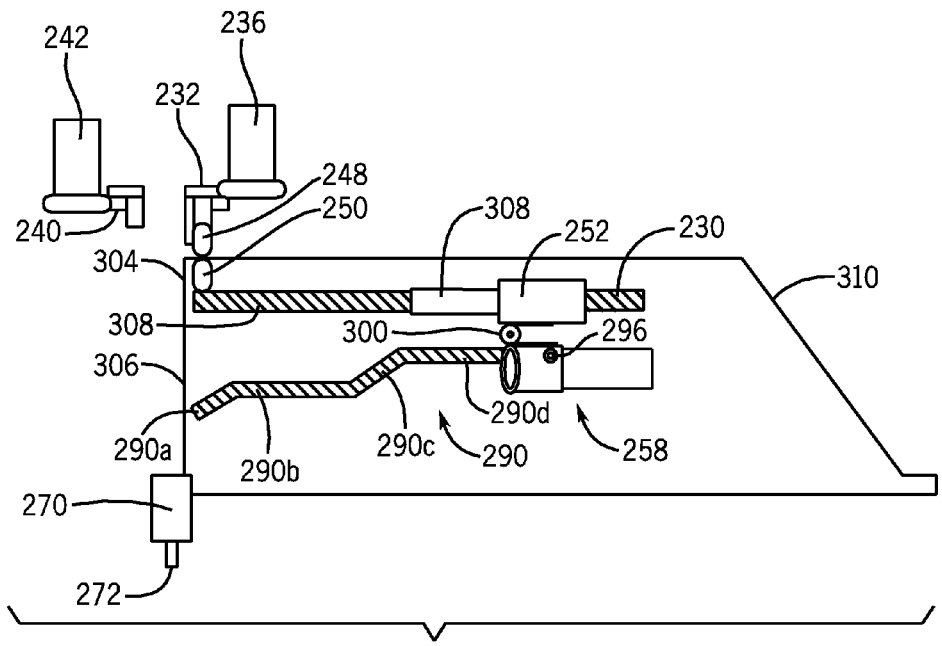
FIG. 17C is a side view illustrating the sample tube of FIG. 17A tilted at an angle of 90° in the centrifuge, in which the sample tube is part way between the load/unload position of the centrifuge and the periphery of the centrifuge, but is closer to the periphery than is the sample tube in FIG. 17B.
Figure 17D:
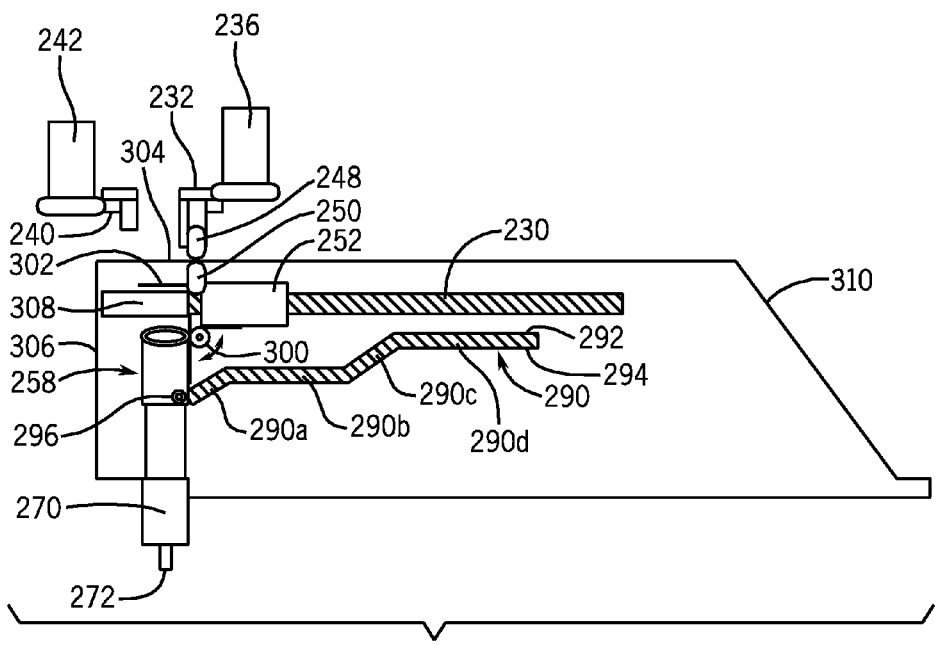
FIG. 17D is a side view illustrating the sample tube of FIG. 17A in the load/unload position of the centrifuge.

An alternative to a magnetic brake is a clamp brake 280, shown in FIGS. 16A and 16B. A clamp brake 280 is a solenoid-driven or motor-driven device having springs 282a, 282b for controlling the gripping force applied to the sample tube holder 260 that surrounds a sample tube when the sample tube is positioned in the sample tube holder 260. The use of springs 282a, 282b ensures that only the force directly provided by the springs 282a, 282b acts on the sample tube holder 260, rather than the force provided directly by the non-resilient gripping arms 284a, 284b driven by the solenoid or the motor. Accordingly, movement of the non-resilient gripping arms 284a, 284b driven by the solenoid or the motor requires a slight amount of over-travel to compress the springs 282a, 282b against the sample tube holder 260. In designing the clamp brake 280, direct gripping of an object by the non-resilient gripping arms 284a, 284b requires precise movement and placement of the non-resilient gripping arms 284a, 284b in conjunction with a precise amount of pressure. Excessive pressure can damage the object held by the non-resilient gripping arms 284a, 284b of the clamp brake 280. In contrast, in designing a clamp brake 280 employing spring compression to allow over-travel, directly gripping a given object by means of springs 282a, 282b requires less precision than does gripping the object by means of direct contact with non-resilient gripping arms 284a, 284b, thereby providing a more predicable gripping force, thus reducing the potential for excessive pressure and eliminating damaging the gripped object.

When actuated, the brake, whether a magnetic brake 270 or a clamp brake 280 prevents the inner race 262b from rotating with the outer race 262a (which rotates at the same speed as does the carousel 202 of the centrifuge 200).

The bearing 262 of the sample tube holder 260 allows the sample tube holder 260 to rotate as the carousel 202 of the centrifuge 200 rotates, at the operating speed of the carousel 202 of the centrifuge 200. However, this situation is not preferred. Because the sample tube holder 260 is attached to the carousel 202 of the centrifuge 200, the sample tube holder 260 rotates at the same velocity as does the carousel 202 of the centrifuge 200. The outer race 262a of the bearing 262 can be connected to the sample tube holder 260. The outer race 262a rotates with the carousel 202 of the centrifuge 200. The inner race 262b is separated from the outer race 262a by low friction bearings 262c. The inner race 262b of the bearing 262 can be connected to or is integral with the sample tube holder 260. Because the inner race 262b and the outer race 262a are separated by low friction bearings 262c, the inner race 262b need not rotate with the outer race 262a. Furthermore, the inner race 262b and the magnetic brake 270 have an interface, or the inner race 262b and the clamp brake 280 have an interface. Thus, the inner race 262b and the sample tube can be maintained in a stationary position by the magnetic brake 270 or the clamp brake 280, while the outer race 262a rotates along with the carousel 202 of the centrifuge 200.

Associated with each lead screw 230 is a track 290 along which the sample tube-holding assembly 258, i.e., sample tube holder 260 and bearing 262, travels. The track 290 for directing a sample tube-holding assembly 258 comprises two parallel guides 292, 294. The guides 292, 294 are made of a corrosion resistant material, e.g., stainless steel, polymeric material. The distance between the parallel guides 292, 294 is sufficient to accommodate a wheel 296, but not so large that the wheel will be of such a size that the wheel creates an imbalance that needs to be cancelled. For that reason, the wheel 296, which can be a cylindrical roller bearing, should be as small as possible and constructed of material of light weight. The wheel 296, that is, the cylindrical roller bearing, can be attached to the sample tube holder 260 by means of a pin, bolt, or rivet. The wheel 296 can be a miniature, sealed bearing, having an aperture in the center thereof, whereby the wheel 260 can be joined to the sample tube holder 260 by means of the aforementioned pin, bolt, or rivet. See, for example, the subject matter accessible by means of the Hypertext Transfer Protocol on the World Wide Web at the website impactbearing.com/miniature_bearing_instrument.html, incorporated herein by reference, for a miniature, sealed bearing suitable for use herein and the subject matter accessible by means of the Hypertext Transfer Protocol on the World Wide Web at the website globalspec.com/Featured Products/Detail/Lantec/SRBN219083_Ring_Bearing/ 15485I/O?fromSpotlight=1, incorporated herein by reference, for a miniature, sealed bearing suitable for use herein.

As shown in FIGS. 17A, 17B, 17C, and 17D, the track 290 has four sections 290a, 290b, 290c, and 290d. The first section 290a is inclined at angle, typically 45°, from the vertical. The second section 290b is perpendicular to the axis of the carousel 202. The third section 290c is inclined at an angle, typically 45°, from the vertical. The fourth section 290d is perpendicular to the axis of the carousel 202. It should be noted that the angle of inclination of the first section 290a and the angle of inclination of the third section 290c need not be inclined at an angle of 45°. When the sample tube-holding assembly 258 is in the second section 290b, the sample tube holder 260 is inclined at an angle of 45° from the vertical position. When the sample tube-holding assembly 258 is in the fourth section 290d, the sample tube holder 260 is perpendicular to the axis of the carousel 202. The angles of inclination of the sample tube holder 260 result from the rotational motion of the carousel 202 of the centrifuge 200 acting upon the sample tube-holding assembly 258.

The initial section 290a of the track 290 closest to the center of the carousel 202 of the centrifuge 200 provides a quick engagement or disengagement of the sample tube holder 260 to the magnetic brake _, thereby preventing the sample tube from rotating at the rotational speed of the carousel 202. The next section 290b of the track 290 adjacent to the initial section 290a of the track 290 provides a fixed tilt angle of 45° from the vertical position for the sample tube and the sample tube holder 260. The next section of the track provides a transition from the tilt angle of 45° from the vertical position to the tilt angle of 90° for the sample tube and the sample tube holder 260 from the vertical position.

FIGS. 17A, 17B, 17C, 17D illustrate various angular positions of one of the twenty-five (25) sample tube holders 260: Load position (0° from the vertical position), 45° from the vertical position (initial separation), 90° from the vertical position (final separation), and unload position (0° from the vertical position). Studies have shown that performing an initial separation when the sample tube holder 260 is inclined at an angle of 45° from the vertical position before a final separation, when the sample tube holder 260 is inclined at an angle of 90° from the vertical position, significantly reduces the length of time required for separation of blood cells from serum or plasma.

Each sample tube-holding assembly 258 is attached to the lead screw nut 252 by a torsion spring 300. The torsion spring 300 is attached to the bearing 262 of the sample tube-holding assembly 258. This torsion spring 300 is wound around a cylindrical hinge pin that allows the sample tube-holding assembly 258 to pivot on the lead screw nut 252. This torsion spring 300 biases the sample tube-holding assembly 258 to a vertical position, but the force of the torsion spring 300 is easily overcome by centrifugal force as the sample tube-holding assembly 258 moves away from the center of the rotating carousel 202 of the centrifuge 200. See, for example, the subject matter accessible by means of the Hypertext Transfer Protocol on the World Wide Web at the website leespring.com/int_learn_torsion.asp, incorporated herein by reference.

A torsion spring 302 and a vertical hinge 304 cooperate to open and close a door 306 that enables the sample tubes to have access to sample tube holders 260. When the door 306 is closed, access to the sample tube-holder 260 is prevented. When the door 306 is pushed open by a rod 308 attached to the lead screw nut 252, access to the sample tube holder 260 is permitted. When the door 306 is opened, the lead screw nut 252 can move, whereby the sample tube-holding assembly 258 can be moved. The door 306 is open when a sample tube is being inserted into a sample tube holder 260. The door 306 is closed when a sample tube is not being inserted into a sample tube holder 260.

A protective enclosure 310, typically made from non-corrosive sheet metal, surrounds each sample tube, sample tube holder 260, lead screw 230, and lead screw nut 252, thereby separating the sample tubes from one another and allowing open sample tubes to undergo centrifugation. The vertical hinge 304 and torsion spring 302 is a part of this protective enclosure 310.

As the sample tube in its sample tube holder 260 move toward the center of the carousel 202, the door 306, which covers the end of the protective enclosure 310, is encountered. The door 306 is resiliently biased to the closed position by means of the torsion spring 302 associated with the hinge 304 of the door 306. The sample tube in its sample tube holder 260 could push the door 306 open by means of its movement toward the center of the carousel 202. However, this act of pushing tends to incline the sample tube holder 260 away from the vertical position. Accordingly, the rod 308 attached to an end of the lead screw nut 252 pushes the door 306 open, while maintaining the sample tube in its sample tube holder 260 in a vertical orientation.

Figure 18:
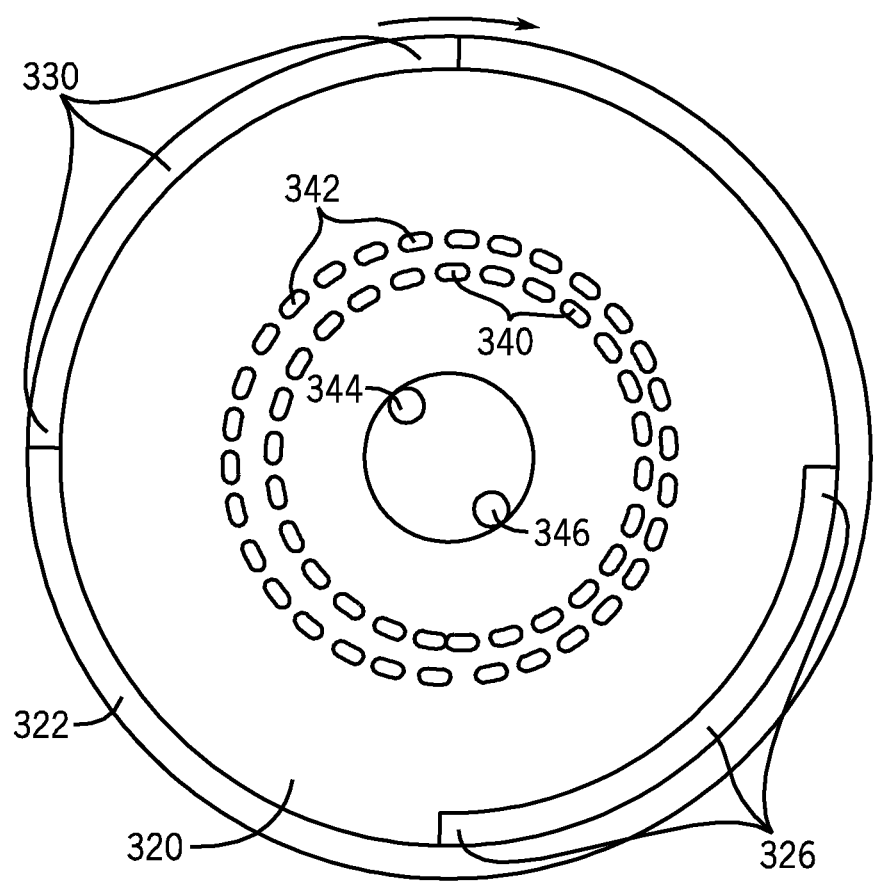
FIG. 18 is a top plan view of the centrifuge of FIG. 11, wherein that portion of the exterior balancing cap overlying the interior balancing cap is cut away. The peripheral portion of the exterior balancing cap is visible in FIG. 18.

Referring now to FIGS. 11 and 18, overlying the upper portion 204 of the carousel 202 are an interior balancing cap 320 and an exterior balancing cap 322. The interior balancing cap 320 forms a close fitting covering for the carousel 202. The exterior balancing cap 322 fits over the interior balancing cap 320. As used herein, the expression "balancing cap" means a rotatable device overlying the carousel 202 of the centrifuge 200, which device is capable of at least contributing to a vector that cancels a vector generated by the rotation of the carousel 202 of the centrifuge 200. Each balancing cap 320, 322 can be rotated about the axis of rotation of the carousel 202 of the centrifuge 200. The interior balancing cap 320 comprises a platform 324 that covers the upper portion 204 of the carousel 202 and a skirt 326 depending from the platform 324, the skirt 326 being perpendicular to the platform 324 of the interior balancing cap 320. The exterior balancing cap 322 comprises a platform 328 that covers the platform 324 of the interior balancing cap 320 and a skirt 330 depending from the platform 328, the skirt 330 being perpendicular to the platform 328 of the exterior balancing cap 322. An arcuate portion of the skirt 326 of the interior balancing cap 320, e.g. from about 90° to about 180°, preferably 120°, is constructed to as to be heavier than the remaining arcuate portion of the interior balancing cap 320. Similarly, an arcuate portion of the skirt 330 of the exterior balancing cap 322, e.g. from about 90° to about 180°, preferably 120°, is constructed to as to be heavier than the remaining arcuate portion of the exterior balancing cap 322. The heavier arcuate portion of each skirt 326, 330 provides the weight that is used for creating a force vector to balance the centrifuge 200. In effect, the heavier arcuate portion of the skirt 326, 330 of each balancing cap 320, 322, respectively, provides an asymmetric weight that can be used to create a corrective force vector, in the same plane, but opposite to the direction of the vector that is causing the centrifuge 200 to be out of balance. When no imbalance vector can be detected, the heavier arcuate portion of the skirt 326 of the interior balancing cap 320 and the heavier arcuate portion of the skirt 330 of the exterior balancing cap 322 can be separated 180° from each other to cancel the effects of their asymmetric weights. Because the skirt 326 of the interior balancing cap 320 is closer to the axis of the carousel 202 than is the skirt 330 of the exterior balancing cap 322, it is preferred that the weight of the interior balancing cap 320 be slightly greater than the weight of the exterior balancing cap 322.

A first set of bearings 340 is interposed between the upper portion 204 of the carousel 202 and the platform 324 of the interior balancing cap 320. A second set of bearings 342 is interposed between the platform 324 of the interior balancing cap 320 and the platform 328 of the exterior balancing cap 322. Bearings that are suitable for this purpose include, but are not limited to, ball bearings, roller bearings, e.g., cylindrical roller bearings. See, for example, the subject matter accessible by means of the Hypertext Transfer Protocol on the World Wide Web at the website globalspec.com/Featured Products/Detail/Lantec/SRBN219083_Ring_Bearing/154851/0?fromSpotlight=1, incorporated herein by reference.

A first stepper motor 344 is provided to rotate the exterior balancing cap 322. A second stepper motor 346 is provided to rotate the interior balancing cap 320.

The first set of bearings 340 allows the platform 324 of the interior balancing cap 320 to rotate in a plane above the upper portion 204 of the carousel 202. The second set of bearings 342 allows the platform 328 of the exterior balancing cap 322 to rotate in a plane above the plane of the platform 324 of the interior balancing cap 320.

Although the interior balancing cap 320 rotates as the carousel 202 rotates, the interior balancing cap 320 can still be moved in small increments with reference to the carousel 202, as required by the balancing technique. Likewise, although the exterior balancing cap 322 rotates as the carousel 202 rotates, the exterior balancing cap 322 can still be moved in small increments with reference to the interior balancing cap 320, as required by the balancing technique.

When the heavier arcuate portion of the interior balancing cap 320 is positioned 180° from the heavier arcuate portion of the exterior balancing cap 322, the effect of the heavier arcuate portion of the interior balancing cap 320 cancels the effect of the heavier arcuate portion of the exterior balancing cap 322. As the position of the heavier arcuate portion of the interior balancing cap 320 changes in relationship to the position of the heavier arcuate portion of the exterior balancing cap 322, i.e., from 180° to a different angle, e.g., 120°, a force vector is created. This force vector is of such a magnitude and direction as to cancel any imbalance(s) resulting from the combined effect of the weights of the sample tubes and the sample tube holders 260 and the distances thereof from the axis of the carousel 202 of the centrifuge 200.

Referring now to FIG. 13, a power source, a central processing unit, and a wireless communication system, such as, for example, WiFi 802.11, Bluetooth 802.15.1, or SimpliciTI 802.15.4, can be located in an area 350 on the lower portion 206 of the carousel 202 of the centrifuge 200. A motor (not shown) can be positioned below the carousel. A sensor 352 for measuring the revolutions per minute of the carousel 202 is positioned on the bearing 354 of the shaft 216. A reference that describes how an optical sensor suitable for use with the centrifuge described herein can be set up is Instruction Manual for the Optical RPM Sensor, Document Version 2.2, Eagle Tree Systems, LLC, (2006), pages 1-4, accessible by means of the Hypertext Transfer Protocol on the World Wide Web at the website eagletreesystems.com, incorporated herein by reference. As the centrifuge is rotated, it generates its own poly-phase AC (alternating current) power, by means of magnetic induction.

A vibration sensor (not shown), can be mounted on the bearing 354 of the shaft 216. The vibration sensor converts a small mechanical movement, i.e., vibration, into an electrical signal that can be interpreted to determine where an imbalance occurs, and the magnitude of the imbalance. The vibration data is collected and analyzed by the central processing unit of the centrifuge 200. Then, a force vector can be calculated for counteracting the imbalance. The force vector is characterized by a direction (within the 360° of rotation) and a magnitude. Through the use of a priori knowledge of the weight(s) of the heavier portions of the balancing caps 320, 322, the movement of the stepper motors 344, 346 for rotating the balancing caps 320, 322, respectively, the movement of the lead screws 230, and the ratio of motor steps to degrees of rotation, a corrective force vector can be calculated and at least one of the balancing caps 320, 322 can be moved into an appropriate position(s). This manner of movement can be continuous or semi-continuous, e.g., once per second. Typically, the vibration sensor is continuously monitored and a new imbalance vector is measured every second (1 second) and a new balancing vector is calculated every second (1 second). The vibration sensor can be a piezoelectric accelerometer. References that describe how a vibration sensor operates can be found in the following references, all of which are incorporated herein by reference:

(a) Balancing machine—Wikipedia, the free encyclopedia, accessible by means of the Hypertext Transfer Protocol on the World Wide Web at the website en.wikipedia.org/wiki/Balancing_machine, incorporated herein by reference.

(b) Accelerometer—Wikipedia, the free encyclopedia, accessible by means of the Hypertext Transfer Protocol on the World Wide Web at the website en.wikipedia.org/wiki/Accelerometer, incorporated herein by reference.

(c) Vibration Sensors—hoffman-balancing.com, accessible by means of the Hypertext Transfer Protocol on the World Wide Web at the website hofmann-balancing.com/products/vibration-sensors.html, incorporated herein by reference.

The major components of the carousel 202 are typically made of die cast aluminum. A material of lighter weight can be considered for the sample tube holders 260, bearings, and lead screws 230, because these components will be exposed to the highest G forces (1500 Gs). These components will not undergo excessive mechanical stress because they are lighter in weight. The weight of the material of lighter weight and the weight of the carousel 202 should be selected so that the combined weight of the sample tubes and the sample tube holders 260 is small, perhaps even insignificant, in comparison to the weight of the rotating carousel 202. This manner of selection will simplify the task of balancing the centrifuge 200. When selecting the individual weights of the sample tubes and the sample tube holders 260, the various distances that the sample tubes and the sample tube holders 260 will range from the axis of the carousel 202 should be taken into account.

After a sealed (or unsealed) sample tube is inserted into a sample tube holder 260 in the centrifuge 200, the sample tube is moved outwardly from the center of the carousel 202 and stopped at the radial position at which the sample tube is inclined at an angle of 45° from the vertical. This position is determined by introducing the value of the weight of the sample tube and the value of the spring constant of the torsion spring illustrated in FIG. _ into the equation $RCF = 0.00001118 \times R \times RPM^2$, where RCF represents the Relative Centrifugal Force (sometimes called G-Force), R represents the distance of the sample tube from the center of the carousel 202 of the centrifuge 200 in centimeters, and RPM represents the revolutions per minute of the carousel 202 of the centrifuge 200 (for example, 2500 revolutions per minute). Thus, the value of RCF at the load position and unload position is zero, because at this position, the distance of the sample tube from the center of the carousel 202 of the centrifuge 200, is zero. The value of RCF at the position where the sample tube holder 260 is inclined at an angle of 45° from the vertical (radial distance from center of centrifuge=10 cm) would be 699, and the value of RCF at the position where the sample tube holder 260 is inclined at an angle of 90° from the vertical (radial distance from center of centrifuge=20 cm) would be 1398. The value of RCF for "VACUTAINER" sample tubes typically ranges from about 1000 to about 1300. Rate of rotation (revolutions per minute) and distances from the center of the carousel 202 of the centrifuge 200 can be selected to optimize the design of the centrifuge 200.

The distance of each sample tube holder 260 from the center of the carousel 202 of the centrifuge 200 can be varied dynamically, i.e., changed as the centrifuge is rotating, to balance the centrifuge, or to maintain the value of RCF constant for a sample tube, while the rate of rotation of the carousel 202 of the centrifuge 200 (in revolutions per minute) varies, as a result of variability in speed of the rotating motor (electric motor, gasoline engine, water wheel, wind mill, bicycle, or hand crank). Variability of rate of rotation (in revolutions per minute) can be reduced by designing the carousel 202 to be a large weight, relative to the combined weights of the tubes and sample tube holders 260, thereby producing the effect of a flywheel. The flywheel effect can be produced when a mechanical device having a significant moment of inertia can be used as a storage device for rotational energy. The mechanical device resists changes in its rotational speed, which aids in stabilizing the rotation of the shaft when a fluctuating torque is exerted upon it. Thus, an object having a high weight, e.g., a carousel, is affected less by a small vibration than an object having a low weight, e.g., a lead screw. Further, although the centrifuge may be dynamically balanced, it is designed such that the combined weight of the sample tube and the sample tube holder 260 is insignificant, relative to the weight of the carousel 202, thereby minimizing any imbalance(s) resulting from the combined effect of the weights of the sample tubes and the sample tube holders 260 and distances thereof from the axis of the carousel 202 of the centrifuge 200.

It should be noted that a minimum number of revolutions per minute will be required to provide the recommended value of RCF to the sample tubes, particularly when the sample tubes are positioned at the maximum possible distance from the axis of the carousel 202 of the centrifuge 200. A typical number for a minimum number of revolutions per minute is 2000.

A spill drain 360 is included in the centrifuge 200 in order to drain liquids that spill from sample tubes. The spilled liquid runs from the spill drain to a container for liquid waste 362.

After the sample tubes are inserted into the centrifuge 200 via the sample tube holders 260, and after centrifugation has begun, if the sample tubes are not properly balanced, an imbalance vector will be detected by a vibration sensor, which transmits information to a central processing unit. As few as zero sample tubes up to as many sample tubes as can be held by the centrifuge 200, i.e., the maximum capacity of the centrifuge 200, can be inserted into the centrifuge 200 before the centrifuge 200 is set in motion. For example, from zero to twenty-five (25) sample tubes can be inserted into a centrifuge 200 that is capable of holding twenty-five (25) sample tubes. For the purpose of this discussion, it has been assumed that each of the sample tube holders of the centrifuge 200 has received a sample tube and the carousel 202 of the centrifuge 200 is rotating at or near a rate of rotation at which centrifugation can be carried out. Several protocols for inserting sample tubes into sample tube holders and removing sample tubes from sample tube holders can be envisioned. In general, it can be assumed that the centrifuge 200 will be operating as sample tubes are being inserted, and the sample tubes are inserted and removed as frequently as every twelve seconds. Assuming that the average centrifugation protocol requires five minutes, 300 sample tubes can be processed by the centrifuge per hour. In summary, twenty-five (25) sample tubes can be inserted while the centrifuge is operating, one sample tube every twelve seconds. After five minutes, one sample tube would have to be removed from a sample tube holder 260 before another sample tube could be inserted into the centrifuge 200.

A vector generated by an imbalance in the centrifuge 200 will have a certain magnitude and direction, e.g., 30 kg, which is equivalent to 20 g at 1500 Gs. In order to balance the centrifuge 200, this vector must be canceled. The vector resulting from the imbalance of the centrifuge 200 is detected and measured by a vibration sensor, which detects unwanted vibration of the centrifuge 200. The vector resulting from the imbalance of the centrifuge can be canceled by moving the interior balancing cap 320, the exterior balancing cap 322, or both the interior balancing cap 320 and the exterior balancing cap 322 in such a manner as to cancel the imbalance vector. The interior balancing cap 320 is moved by a stepper motor. The exterior balancing cap 322 is moved by a stepper motor. Signals to the interior balancing cap 320 and the exterior balancing cap 322 are initiated by the central processing unit upon receipt of data from the vibration sensor. The amount of movement of the interior balancing cap 320 and the exterior balancing cap 322 is determined by a balancing algorithm. A vector for canceling the vector resulting from the imbalance of the centrifuge 200 is created by modifying the distance between a sample tube and the axis of the carousel 202 of the centrifuge 200. This modification of distance is continuous (i.e., dynamic), typically at a rate of one movement of the stepper motor per second. A movement of the stepper motor can involve one or more steps of the stepper motor. A preferred frequency for sampling the vibration sensor and adjusting the balancing caps is once per second. A reasonable frequency for sampling the vibration sensor and adjusting the balancing caps ranges from about one time per second to about ten times per second.

When the first sealed (or unsealed) sample tube is inserted into a sample tube holder 260 in the centrifuge 200, the next sealed (or unsealed) sample tube is loaded in a sample tube holder 260 in an opposing position in the centrifuge 200 (180° to aid in balancing the centrifuge 200 and minimize the magnitude of balancing required. By calculating the RCF vector for the entire centrifuge 200 after a given sample tube has been inserted into the centrifuge 200, the appropriate location for the next sample tube can be selected to minimize the resultant RCF vector. Thus, the algorithm for balancing the centrifuge 200 is dynamic; the algorithm recalculates the next successive load position after each sample tube is inserted into a sample tube holder 260 of the centrifuge 200 or removed from a sample tube holder 260 of the centrifuge 200. Only one sample tube holder 260 in the centrifuge 200 can be positioned for receiving a sample tube or giving up a sample tube at any given time. Operations for inserting sample tubes into the centrifuge 200 and removing sample tubes from the centrifuge 200 can be coordinated with the other robotic controllers in the system by means of a wireless interface, thereby ensuring optimal throughput, optimal time to result, and sufficient time to carry out the operations of the centrifuge 200. FIG. 13 illustrates that wireless communication can be provided to other robotic controllers by means of the bottom portion of the carousel 202.

Figure 19A:
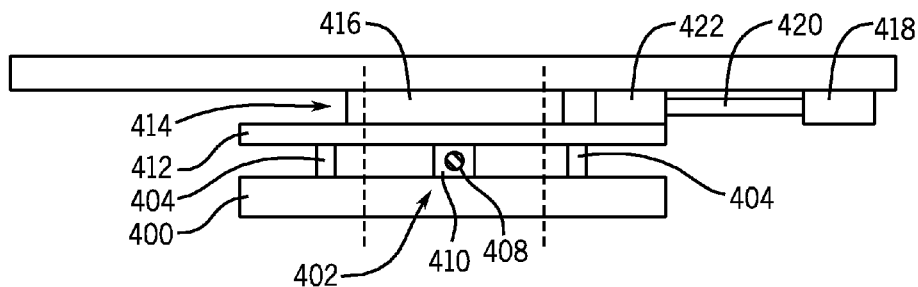
FIG. 19A is a side view of an assembly comprising two positioning mechanisms and a balancing weight for cancelling imbalance vectors generated by a centrifuge.
Figure 19B:
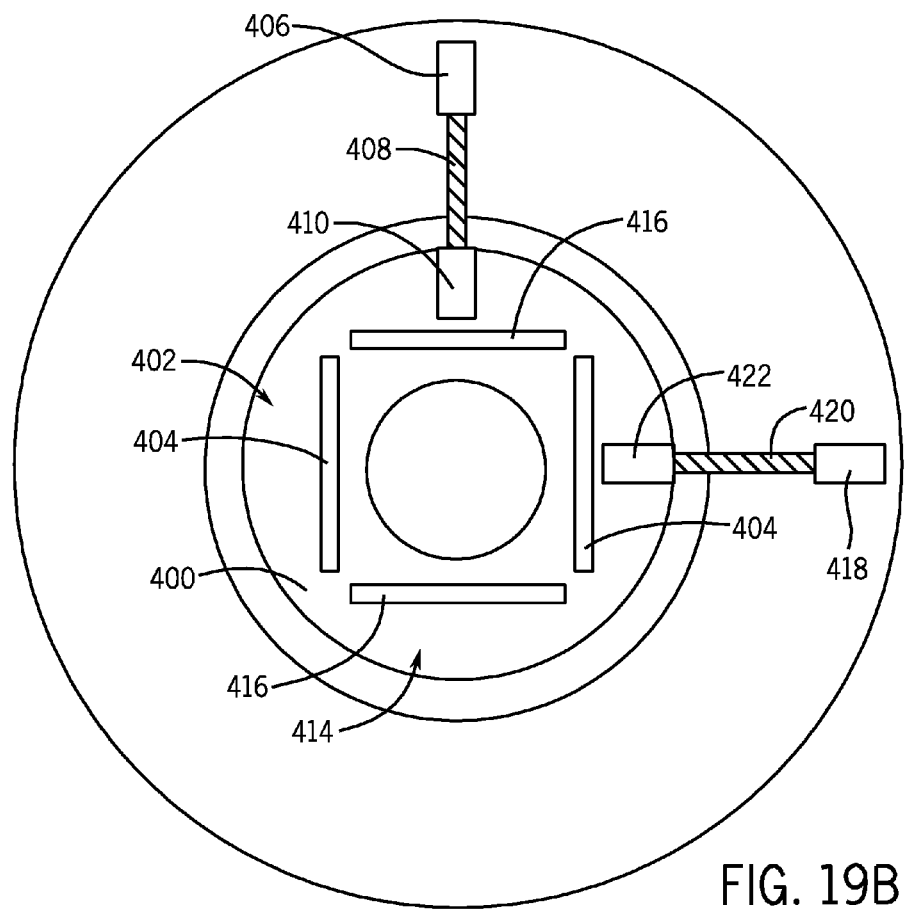
FIG. 19B is a top plan view of the assembly of FIG. 19A.

An alternative balancing technique is shown in FIGS. 19A and 19B. As in the embodiment shown in FIG. 11, the embodiment using the balancing technique shown in FIGS. 19A and 19B and described below utilizes the following components:
(1) centrifuge 200 comprising a carousel 202 having an upper portion 204 and a lower portion 206;
(2) plurality of rotor coils 208 mounted on the lower portion 206 of the carousel 202;
(3) plurality of field coils 212 mounted around the periphery of the lower portion 206 of the carousel 202;
(4) upper portion 204 of the carousel 202 including a plurality of lead screws 230, each lead screw 230 capable of having a sample tube associated therewith;
(5) lead screw nut 252 mounted upon each lead screw 230 and that can traverse the lead screw 230 when the lead screw 230 is actuated;
(6) sample tube-holding assembly 258, which comprises a sample tube holder 260 and a bearing 262, attached to each lead screw nut 252 by means of a torsion spring;
(7) sample tube-holding assembly 258 further including a reflector 264;
(8) plurality of emitter-detectors 266; and
(9) brake system, e.g., magnetic brake system, clamp brake system.

In addition to the aforementioned major components, auxiliary components of the types mentioned earlier with respect to the centrifuge employing balancing caps can also be included. These auxiliary elements include, but are not limited to, vibration sensor, sensor for counting revolutions per minute.

This embodiment employs a balancing weight 400. The balancing weight 400 is attached to and supported by a first positioning mechanism 402 comprising at least one bearing 404, e.g., slide bearing, ball slide bearing. Such an arrangement allows the balancing weight 400 to be moved by a first stepper motor 406 via a lead screw 408 and lead screw nut 410. The first positioning mechanism 402 to which the balancing weight 400 is attached is attached to an element 412 interposed between the first positioning mechanism 402 and a second positioning mechanism 414. The second positioning mechanism 414 comprises at least one bearing 416, e.g., slide bearing, ball slide bearing. The at least one bearing of the first positioning mechanism 402 is perpendicular to the at least one bearing of the second positioning mechanism 414. The at least one bearing of the second positioning mechanism 414 is attached to and supported by the carousel 202 of the centrifuge 200. The function of the element 412 interposed between the first positioning mechanism 402 and the second positioning mechanism 414 is to provide a connection between the first positioning mechanism 402 and the second positioning mechanism 414. The balancing weight 400 is moved in a direction perpendicular to the movement of the element 412 by a second stepper motor 418 via a lead screw 420 and a lead screw nut 422. It should be noted that the first positioning mechanism 402 can be separated from the second positioning mechanism 414 by an angle other than 90°. However, if the first positioning mechanism is not perpendicular to the second positioning mechanism, more than two positioning mechanisms may be required.

Thus, by using a first positioning mechanism 402 comprising at least one bearing 404, and a second positioning mechanism 414 comprising at least one bearing 416, a first stepper motor 406 and a lead screw 408 actuated thereby and a second stepper motor 418 and lead screw 420 actuated thereby, the lead screw 408 being perpendicular to the lead screw 420, the balancing weight 400 can be positioned by movement in two directions in the same plane, one direction being perpendicular to the other direction. After an imbalance vector is detected, by moving the balancing weight 400 to a particular position, the imbalance vector can be negated. A bore can be formed in the balancing weight 400 in order accommodate the shaft 216 and a magnetic brake, if that is the type of brake used. More than two positioning mechanisms can be used. However, the use of more than two positioning mechanism is not preferred, because such use increases the complexity of the system.

United States Patent Application Publication No. US 2008/0024301 A1 discloses ball slide bearings for providing controllable positioning of the balancing weight in a first direction and controllable positioning of the balancing weight in a second direction. Because movement in each direction uses a separate positioning mechanism, the positioning mechanisms can be moved independently and simultaneously. See, for example, the subject matter accessible by means of the Hypertext Transfer Protocol on the World Wide Web at the website pbclinear.com/Low-Profile-Uni-Guide, incorporated herein by reference.

Figure 20A:
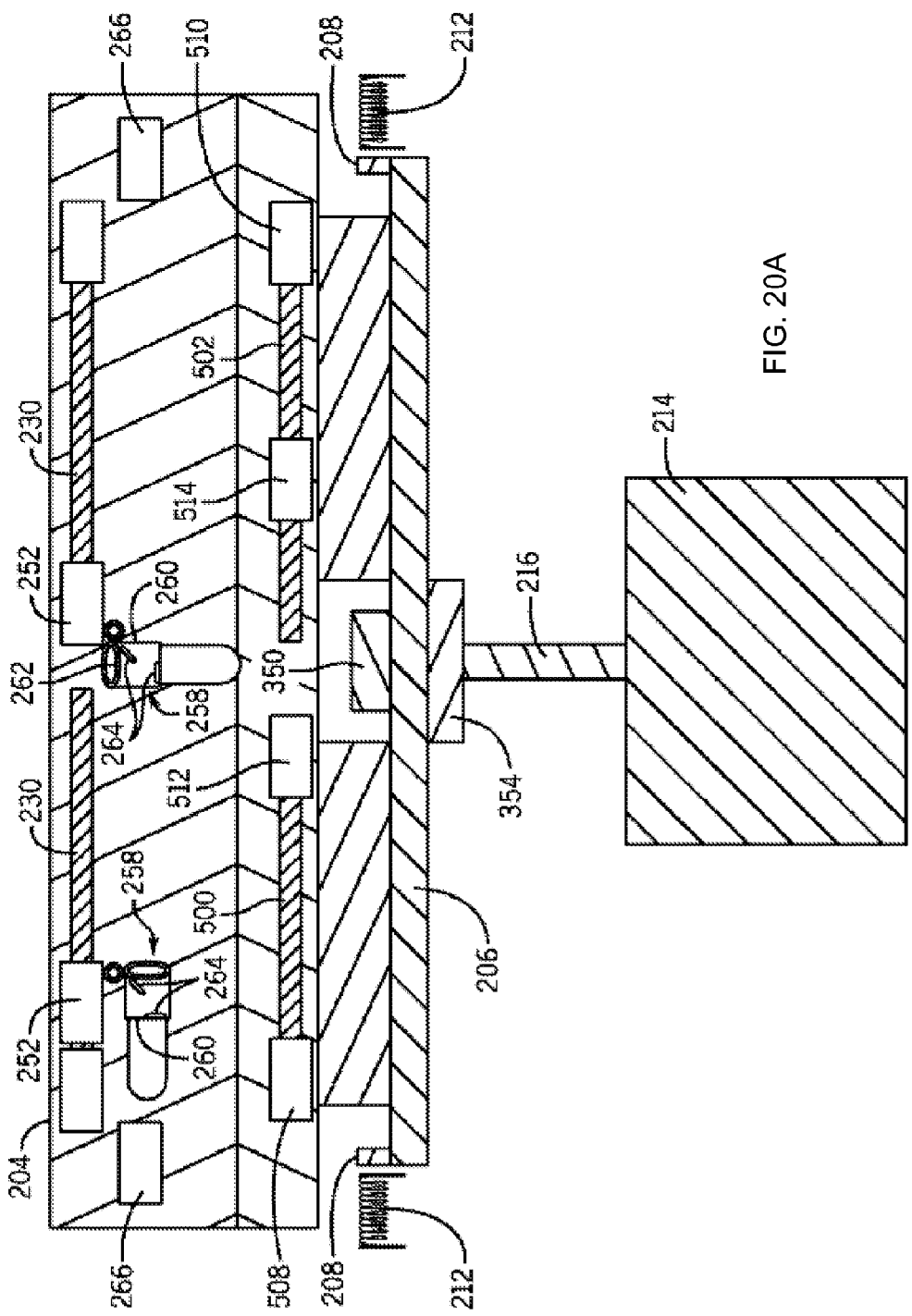
FIG. 20A is a cross-sectional view of another embodiment of a centrifuge described herein. In this embodiment, the balancing weights, each of which is mounted on a lead screw, are employed to for cancelling imbalance vectors generated by the centrifuge.
Figure 20B:
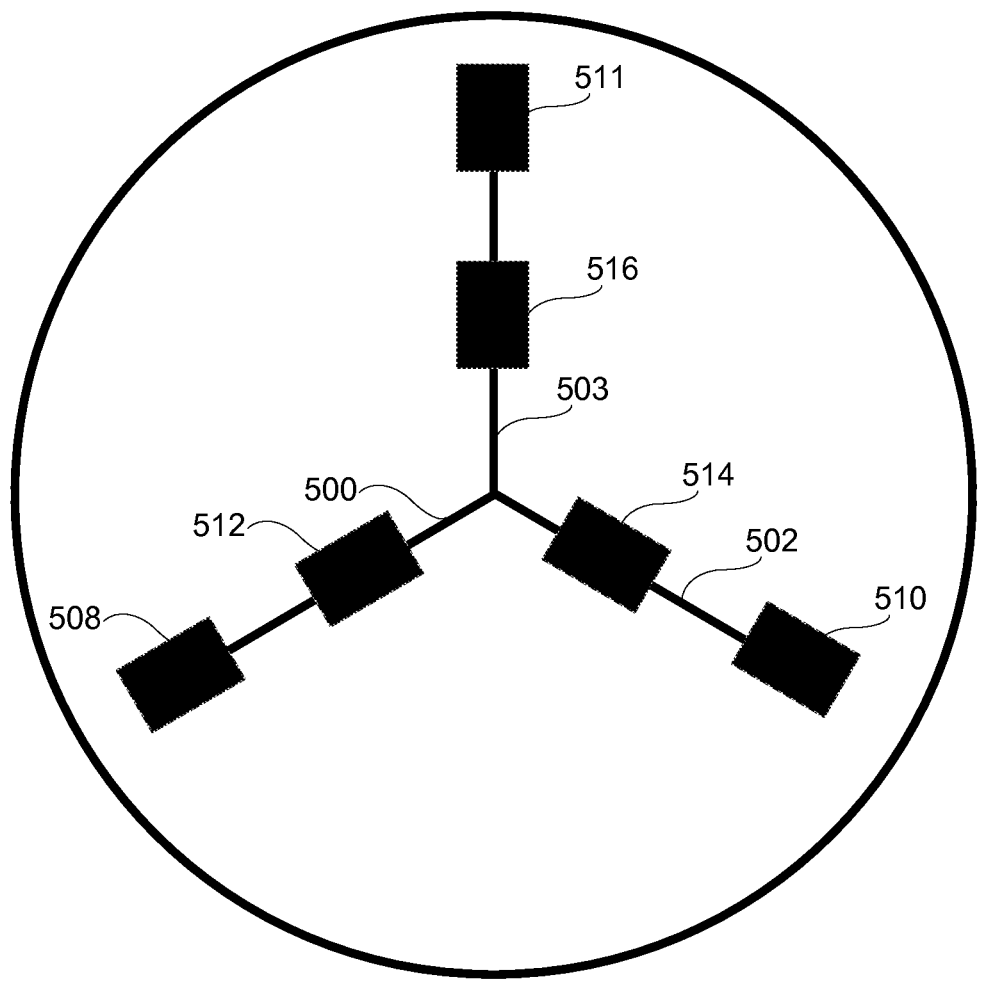
FIG. 20B is a top plan view of a block diagram of elements of the centrifuge of FIG. 20A.

Another alternative balancing technique is shown in FIGS. 20A and 20B. As in the embodiment shown in FIG. 11, the embodiments using the balancing technique shown in FIGS. 20A and 20B and described below utilize the following components:
(1) centrifuge 200 comprising a carousel 202 having an upper portion 204 and a lower portion 206;
(2) plurality of rotor coils 208 mounted on the lower portion 206 of the carousel 202;
(3) plurality of field coils 212 mounted around the periphery of the lower portion 206 of the carousel 202;
(4) upper portion 204 of the carousel 202 including a plurality of lead screws 230, each lead screw 230 capable of having a sample tube associated therewith;

(5) lead screw nut 252 mounted upon each lead screw 230 and that can traverse the lead screw 230 when the lead screw 230 is actuated;

(6) sample tube-holding assembly 258, which comprises a sample tube holder 260 and a bearing 262, attached to each lead screw nut 252 by means of a torsion spring;

(7) sample tube-holding assembly 258 further including a reflector 264;

(8) plurality of emitter-detectors 266; and (9) brake system, e.g., magnetic brake system, clamp brake system.

In addition to the aforementioned major components, auxiliary components of the types mentioned earlier with respect to the centrifuge employing balancing caps can also be included. These auxiliary elements include, but are not limited to, vibration sensor, RPM sensor.

In FIGS. 20A and 20B, each balancing element is a balancing nut that can be moved along a lead screw. At least three balancing nuts are required for this embodiment in order to negate an imbalance vector. FIG. 20A shows two balancing nuts and FIG. 20B is a top plan view of a block diagram of elements of an example centrifuge showing three balancing nuts. A first lead screw 500 and a second lead screw 502 are separated from each other by 120°. A third lead screw 503 (shown in FIG. 20B) is separated from the lead screw 500 by 120° and is further separated from the lead screw 502 by 120°. The first lead screw 500 rotates within a first bearing (not shown), the second lead screw 502 rotates within a second bearing (not shown), and the third lead screw 503 rotates within a third bearing (not shown). The first lead screw 500 is actuated by a first stepper motor 508 positioned at the end of the first lead screw opposite to the end where the bearing is positioned. The second lead screw 502 is actuated by a second stepper motor 510 positioned at the end of the second lead screw opposite to the end where the bearing is positioned. The third lead screw 503 is actuated by a third stepper motor 511 positioned at the end of the second lead screw opposite to the end where the bearing is positioned. After an imbalance vector is detected, by moving a first balancing nut 512, a second balancing nut 514, a third balancing nut 516, or two or more of the balancing nuts 512, 514, 516 to particular positions, the imbalance vector can be negated. Alternatively, more than three assemblies of lead screw, bearing, stepper motor, and balancing nut can be used. The use of three assemblies of lead screws, bearings, stepper motors, and balancing nuts appears to be the most efficient and the most economical arrangement.

Sample tubes can be introduced in the center of the centrifuge 200, while the centrifuge is rotating at any speed (e.g., up to 2500 revolutions per minute). The sample tubes can be collection tubes or aliquot tubes. The rotational motion of the centrifuge 200 can be brought about by any source of power, such as, for example, an electric motor, a gasoline engine, a water wheel, a wind mill, a bicycle, or a hand crank. Accordingly, the centrifuge 200 can be used in both developing countries and in developed countries.

Figure 21:
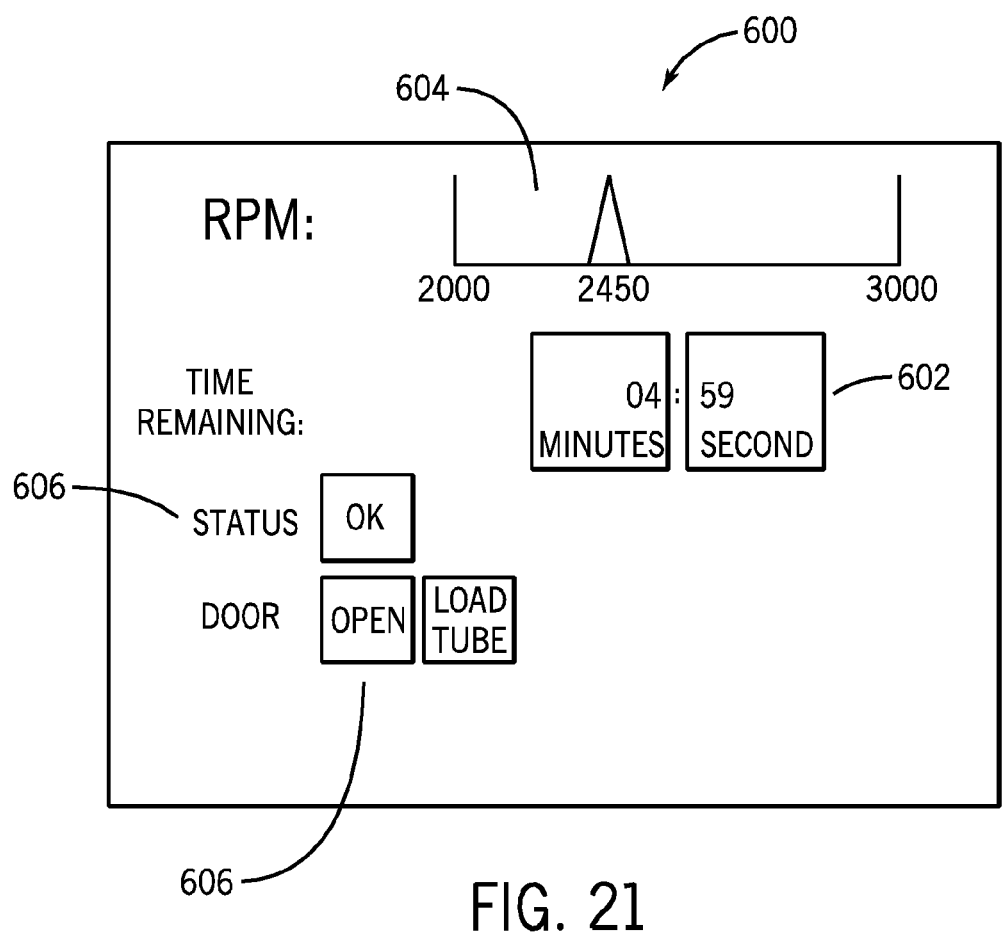
FIG. 21 is a front view of a display for monitoring various parameters of a centrifuge.

In the embodiments of the centrifuge described herein, the alternating current energy resulting from the field coils is rectified to direct current energy and regulated by a source of power positioned upon the carousel 202. This source of power provides sufficient energy for a central processing unit, for a controller for robotics, and for transmission and reception of wireless signals to other controllers for robotics, central processing units, etc. If desired, power can be provided from a position off the carousel 202 to provide energy for other functions when electricity is not available. Examples of other functions include, but are not limited to, loading sample tubes, loading robotic devices, running displays and controls of user interfaces, running the control center of the system, charging UPS batteries. If a meter for measuring revolutions per minute is available, a display can be provided to indicate the speed of rotation of the carousel of the centrifuge. In developing countries, when electricity may not be available, this display can be used to "regulate" a person using a hand crank or bicycle. FIG. 21 shows such a display 600, which provides the operator with a countdown clock 602, a speed indicator 604, and a plurality 606 of status conditions.

OPERATION

In order to operate the system, an operator of the system or the provider of the system will review the workflow requirements of the laboratory, and estimate the required throughput, as well as the number of analyzers and tests and/or assays available for testing purposes. The configuration of the system will be set to meet the majority of the workflow requirements of the laboratory. The operator of the system or a Laboratory Information System (LIS) will download test orders to the system for samples that will eventually be presented to the system for testing. The operator of the system or a robotic system will load the required disposable/consumable items onto the system. The operator of the system or the Laboratory Automation System (LAS) will present the required samples to the system. The system will automatically perform closed tube sampling, dispense whole blood samples into a hematology analyzer, separate aliquot(s) of the sample for immunoassay testing or clinical chemistry testing, and dispense serum or plasma into an immunoassay analyzer and/or clinical chemistry analyzer. The system will determine and report the results of an analysis of blood, or an antigen or other analyte in a sample, according to the downloaded test order for that sample. The operator of the system or the LAS will remove the samples from the system. The operator of the system or the LIS will review and release test results to the originator of the test order.

The following non-limiting examples illustrate operations of the various sampling systems described herein. The following examples generally employ systems of the type shown in FIG. 9, along with removal of modules not specified.

EXAMPLE 1

Operation of a Closed Tube Sampling System

A versatile embodiment of a closed tube sampling system includes one hematology analyzer, one immunoassay analyzer, one clinical chemistry analyzer, one sample tube aspirating module, and an agglutination reagent addition module. See FIG. 9. An operator loads sample tube carriers holding sample collection tubes having stoppers and containing samples of whole blood that have not undergone centrifugation. The robotic sample handler prioritizes carriers holding sample collection tubes for STAT assays ahead of carriers containing sample collection tubes for routine assays. The barcode reader of the closed tube sampling system reads the barcodes on the sample collection tubes, detects the presence of stoppers on the sample collection tubes, if any, the stoppers on the sample collection tubes (if required), and transfers a specified volume of sample to an aliquot tube. The sample tube carrier can then be removed from the system. The sample in the aliquot tube is routed for testing. A typical route can be described as follows: (1) first to the hematology analyzer, (2) then to the agglutination reagent addition module, (3) then to the immunoassay analyzer and the clinical chemistry analyzer, where separation is carried out by means of magnetic fields before the aliquot tube is positioned for receiving a sample that has been aspirated.

With respect to immunoassay analyzers and clinical chemistry analyzers, a sample aspirating probe is inserted into the aliquot tube and a portion of the sample is aspirated. In essence, the sample aspirating probe of the analyzer reads the aliquot tube as an open "plasma/serum" sample tube; accordingly, no modification of the analyzer is required. Further, the aliquot tube is retained for retesting (immunoassay testing and clinical chemistry testing only), and then disposed if and when results indicate that no retesting required. The operator can load samples of small volume by means of individual sample cups. Interaction with the system by the operator is required for positive identification of a sample at a location for STAT assays. Because sample cups typically do not have barcodes, the operator is required to enter certain data to ensure that the sample being drawn from the sample tube is the sample for which tests have been ordered (i.e., positive identification of a sample). Calibrations for assays can be performed at the analyzers by means of Local Sample Handlers. A Local Sample Handler is a device, e.g., a small carousel, for loading and unloading sample at each clinical analyzer or hematology analyzer. A Local Sample Handler is typically used for STAT samples, controls, calibrators. The functions of the closed tube sampling system can be carried out within the hematology analyzer.

Thus, a specified portion of the sample aspirated from the sample tube for hematology testing can be transferred into a sample tube, then routed to an agglutination reagent addition module, then to an immunoassay analyzer and a clinical chemistry analyzer, where separation can be performed by means of magnetic fields prior to and while the sample tube is positioned for aspiration.

EXAMPLE 2

Operation of a Closed Tube Sampling System

FIG. 9 illustrates an embodiment of a closed tube sampling system that has one hematology analyzer, one immunoassay analyzer, one clinical chemistry analyzer, and one sample tube aspirating module.

In order to operate the system, the operator of the system loads sample tube carriers having sample collection tubes having stoppers and containing uncentrifuged samples of whole blood. The robotic sample handler prioritizes sample tube carriers holding sample collection tubes for STAT assays ahead of sample tube carriers containing sample collection tubes for routine assays. A barcode reader reads the barcodes on the sample collection tubes, detects the presence of stoppers on the sample collection tubes, if any, a piercing element pierces the stoppers on the sample collection tubes (if required) or a cutting blade cuts slits in the stoppers (if required), and a specified volume of sample is transferred to an aliquot tube. The sample tube carrier can then be removed from the system. The sample in the aliquot tube is routed for testing. A typical route can be described as follows: (1) first to the hematology analyzer, (2) then to the immunoassay analyzer and clinical chemistry analyzer, where separation is carried out by means of a selected separation technique, such as for example, ultrasonic waves, before the aliquot tube is positioned for receiving a portion of a sample that has been aspirated.

Subsequently, the sample aspirating probe is inserted into the aliquot tube and a portion of the sample is aspirated. In essence, the sample aspirating probe of the analyzer reads the aliquot tube as an open "plasma/serum" sample tube; accordingly, no modification of the analyzer is required. Further, the sample tube is retained for retesting (immunoassay testing and clinical chemistry testing only), and then disposed if and when results indicate that no retesting required. The operator can load samples of small volume by means of individual sample cups. Interaction with the system by the operator is required for positive identification of a sample at a location for STAT assays. Because sample cups typically do not have barcodes, the operator is required to enter certain data to ensure that the sample being drawn from the sample tube is the sample for which tests have been ordered (i.e., positive identification of a sample). Calibrations for assays are performed at the analyzers by means of Local Sample Handlers. The functions of the closed tube sampling system can be carried out within the hematology analyzer.

Thus, a specified portion of the sample aspirated from the aliquot tube for hematology testing can be transferred into a sample tube, then routed to an immunoassay analyzer and a clinical chemistry analyzer, where separation can be performed by means of magnetic fields prior to and while the sample tube is positioned for aspiration.

EXAMPLE 3

Operation of a Closed Tube Sampling System

FIG. 9 illustrates an embodiment of a closed tube sampling system that includes one hematology analyzer, one immunoassay analyzer, one clinical chemistry analyzer, one sample tube aspirating module, and a continuous access centrifugation module. In order to operate the system, the operator loads sample tube carriers holding sample collection tubes having stoppers and containing uncentrifuged samples of whole blood. The robotic sample handler prioritizes sample tube carriers holding sample collection tubes for STAT samples ahead of sample tube carriers holding sample collection tubes for routine analyses. A barcode reader reads the barcodes on the sample collection tubes, detects the presence of stoppers on the sample collection tubes, if any, a piercing element pierces the stoppers of the sample collection tubes (if required) or a cutting blade forms slits in the stoppers (if required), and a specified volume of sample is transferred to an aliquot tube. The sample tube carrier can then be removed from the system. The sample is routed for testing. A typical route can be described as follows: (1) first to the hematology analyzer, (2) then to the continuous access centrifugation module (where the open sample tube can optionally be sealed with a foil and separation is performed), (3) then to the immunoassay analyzer and clinical chemistry analyzer, where the appropriate assays are performed.

In essence, the sample aspirating probe of an immunoassay analyzer or a clinical chemistry analyzer reads the sample tube as an open "plasma/serum" sample tube; accordingly, no modification of the analyzer is required. Further, the aliquot tube is retained for retesting (immunoassay testing and clinical chemistry testing only), and then disposed when results indicate that no retesting is required. The operator can load samples of small volume by means of individual sample cups. Interaction with the system by the operator is required for positive identification of a sample at a location for STAT samples. Because sample cups typically do not have barcodes, the operator is required to enter certain data to ensure that the sample being drawn from the sample tube is the sample for which tests have been ordered (i.e., positive identification of a sample). Calibrations for assays are performed at the analyzers by means of Local Sample Handlers. The functions of the closed tube sampling module can be carried out within the hematology analyzer.

Thus, a specified portion of the sample aspirated from the sample tube for hematology testing can be transferred into a sample tube, then routed to the centrifuge, where separation can be performed before the sample tube is positioned for aspirating the sample, then to the immunoassay analyzer, and clinical chemistry analyzer.

The integration of hematology testing, immunoassay testing, and clinical chemistry testing as described herein requires only one sample collection tube. Typically, anti-coagulants are placed in sample tubes to prevent the blood from clotting, because clotting interferes with aspiration of the sample and the methods of testing. Anti-coagulants for hematology have evolved separately from anti-coagulants for immunoassay testing and clinical chemistry testing, because separation of cells is paramount to the cell counting performed for hematology. In addition, hematology analyses often employ slides for performing blood smear analyses, and anti-coagulants must not stain or discolor the cells in the blood smear. Anti-coagulants for immunoassay testing and clinical chemistry testing are selected not only to prevent clotting, but also to avoid adversely affecting the analytes of blood chemistry analyses (such as calcium, iron, potassium, etc.).

As a result, anti-coagulants for hematology testing and anti-coagulants for immunoassay testing and clinical chemistry testing, although similar in function, are distinctly different.

Various types of anti-coagulants are described below.

1 Direct Thrombin Inhibitors include, but are not limited to, Argatroban, Bivalirudin, Dabigatran, Hirudin, Ximelagatran. Heparins include, but are not limited to Ardeparin sodium, Bemiparin sodium, Certoparin sodium, Dalteparin sodium, Danaparoid sodium, Enoxaparin sodium, Fondaparinux sodium, Heparin, Idraparinux sodium, Low Molecular Weight Heparin, Parnaparin sodium, Reviparin sodium, Tinzaparin sodium.

2. Vitamin K Antagonists include, but are not limited to, Acenocoumarol, Brodifacoum, Coumatetralyl, Dicoumarol, Phenindione, Phenprocoumon, Pindone, Tioclomarol, Warfarin.

3. Outside the body Heparins include, but are not limited to, sodium heparins or lithium heparins provided in "VACUTAINER" brand test tubes having green stoppers.

4. Chelating agents include, but are not limited to, ethylenediaminetetraacetic acid (EDTA), citrate mild chelating agent, usually trisodium citrate, anticoagulant citrate dextrose, citrate phosphate dextrose or citrate-phosphate-dextrose-adenine.

5. Oxalate is a mild chelating agent, and the anticoagulant used in fluoride provided in "VACUTAINER" brand test tubes having green stoppers.

The systems described herein reduce biological hazards to operators, reduces repetitive motion injuries to operators, maintains throughput or assay performance of existing analyzers, reduces hazards to operators resulting from stopper cutting "sharps" by containing all sharps in a holder, and reduces service maintenance required for replacement of worn sharps.

The systems described herein significantly reduce the labor required for sorting samples, balancing and centrifugation. The systems significantly reduce the time needed to obtain a result by integrating the blood separation step into the analyzer system/work cell. The systems enable a fully automated method for processing a single sample collection tube for hematology testing, immunoassay testing, and clinical chemistry testing, while providing high throughput for large laboratories that process many samples. The systems enable random and continuous access processing of assays, along with handling STAT samples. These benefits can be realized with current automated analyzers without requiring new analyzers to be developed.

This systems described herein require patients and phlebotomists to provide only one sample tube for hematology testing, immunoassay testing, and clinical chemistry testing, thereby reducing patient distress, reducing sample collection costs, reducing inventory costs (to stock more than one type of sample tube), and reducing solid waste disposal costs (sample tubes often account for the majority of laboratory solid waste). The centrifuge eliminates "batches", and any subsequent delays for processing STAT samples. The centrifuge provides the ability accept energy from sources other than electrical sources, such as hand cranks, bicycles, windmills, waterwheels, etc., thereby allowing modern centrifugation techniques to be performed in developing countries.

The continuous access centrifuge described herein provides several advantages for integrating hematology testing, immunoassay testing, and clinical chemistry testing. These advantages include, but are not limited to, high throughput, ease of introducing STAT samples, ease of sorting and automatic balancing, and total integration of the various tests. The throughput of the continuous access centrifuge can reach 300 samples per hour, thereby meeting the throughput requirements for the largest "ARCHITECT" multi-module system configuration that is integrated with a hematology analyzer. Because batch type centrifuges cannot provide continuous access, once a centrifugation process is started, the centrifuge is unavailable for up to 10 minutes. Accordingly, a STAT sample delivered from an emergency room cannot be loaded into a batch type centrifuge while the centrifuge is revolving. Batch type centrifuges require the buckets of the centrifuge to be balanced prior to the centrifugation operation, with the result that the time of the centrifugation process is extended and results from patients are delayed. A continuous access centrifuge can provide total automation to a laboratory by integrating hematology analyzer(s), immunoassay analyzer(s), and clinical chemistry analyzer(s).

Various modifications and alterations of this invention will become apparent to those skilled in the art without departing from the scope and spirit of this invention, and it should be understood that this invention is not to be unduly limited to the illustrative embodiments set forth herein.

What is claimed is:
1. A centrifuge comprising:
a carousel having an upper portion and a lower portion, the upper portion of the carousel defining an opening therein to receive a first sample tube;
a first track and a second track;
a first drive mechanism attached to the upper portion of the carousel;
a second drive mechanism attached to the upper portion of the carousel;
a first movable element mounted to the first drive mechanism, the first movable element to traverse the length of the first drive mechanism when the first drive mechanism is actuated;
a second movable element mounted to the second drive mechanism;

a first sample tube-holding assembly comprising a first sample tube holder to receive the first sample tube, the first sample tube-holding assembly coupled to the first movable element;

a second sample-tube holding assembly comprising a second sample tube holder to receive a second sample tube, the second sample tube-holding assembly coupled to the second movable element, wherein the first drive mechanism is slidably coupled to the first track and the second drive mechanism is slidably coupled to the second track, wherein the first sample tube holder is to receive the first sample tube when the first sample tube holder is in a first position and to carry the first sample tube along the first track via the first drive mechanism to a second position, and wherein the second sample tube holder is to receive a second sample tube when the second sample tube holder is a third position and to carry the second sample tube along the second track via the second drive mechanism to a fourth position, wherein at least one of the first sample tube holder or the second sample tube holder moves between the first position and the second position or the third position and the fourth position, respectively, during rotation of the carousel; and a balancing element spaced apart from the first sample-tube holding assembly and the second sample-tube holding assembly to stabilize the carousel during rotation of the carousel.

2. The centrifuge of claim 1, wherein in the first position, the first sample tube holder is vertically oriented and in the second position, the first sample tube holder is horizontally oriented and wherein in the third position, the second sample tube holder is vertically oriented and in the fourth position, the second sample tube holder is horizontally oriented.

3. The centrifuge of claim 1, wherein the first sample tube holder is at least partially encased in a first bearing and the second sample tube holder is at least partially encased in a second bearing, the first bearing and the second bearing to rotate the first sample tube holder and the second sample tube holder, respectively, during rotation of the carousel.

4. The centrifuge of claim 1, further comprising a first lead screw to move the first sample tube holder along the first track and a second lead screw to move the second sample tube holder along the second track, the first lead screw controlled by the first drive mechanism and the second lead screw controlled by the second drive mechanism.

5. The centrifuge of claim 4, wherein the first sample tube holder is coupled to the first lead screw via a first torsion spring and the second sample tube holder is coupled to the second lead screw via a second torsion spring.

6. The centrifuge of claim 4, wherein the first drive mechanism is to move the first sample tube holder to a radial position between the first position and the second position, wherein in the radial position, the first sample tube is oriented at an incline.

7. The centrifuge of claim 6, wherein the radial position is determined based on at least one of a weight of the first sample tube, a spring constant of the first torsion spring, or a distance of the first sample tube from a center of the carousel.

8. The centrifuge of claim 1, wherein the first position and the third position are proximate to a center of the carousel.

9. The centrifuge of claim 8, further comprising a brake disposed proximate to a center of the carousel, the brake to prevent the first sample tube holder and the second tube holder from rotating when the first sample tube holder and the second sample tube holder are in first position and the third position respectively.

10. The centrifuge of claim 8, wherein the first position and the third position are coextensive.

11. The centrifuge of claim 1, wherein the first track and the second track comprise two parallel guides, and wherein a distance between the parallel guides of the first track and the second track is to accommodate the first sample tube holder and the second sample tube holder.

12. The centrifuge of claim 1, wherein the first track and the second track are radially separated about an axis of rotation of the carousel.

13. The centrifuge of claim 1, further comprising a spill drain to collect liquids spilling from the sample tubes during rotation of the carousel.

14. The centrifuge of claim 1, wherein the first sample tube is positionable in the first position at substantially the same time the second sample tube is positionable in the fourth position during rotation of the carousel.

15. The centrifuge of claim 14, wherein the first position and the third position are proximate to a center axis of the carousel.

16. The centrifuge of claim 14, wherein the second position and the fourth position are separated a radial distance about an axis of rotation of the carousel.

17. The centrifuge of claim 1, wherein the balancing element is to counterbalance an imbalance generated by the first sample tube and the second sample tube during rotation of the carousel.

18. The centrifuge of claim 1, wherein the first sample tube holder and the second sample tube holder comprise respective protective enclosures, the respective protective enclosures to separate the first sample tube holder from the second sample tube holder.

19. The centrifuge of claim 1, wherein movement of the first sample tube holder between the first position and the second position and movement of the second sample tube holder between the third position and the fourth position is continuous for a duration of the rotation of the carousel.

20. The centrifuge of claim 1, wherein the first position is a delivery position and the fourth position is a processing position, and wherein the first sample tube holder is in the delivery position when the second sample tube holder is in the processing position.

21. The centrifuge of claim 1, wherein the first sample tube holder is to carry the first sample tube between the first position and the second position independently of the second sample tube holder carrying the second sample tube holder between the third position and the fourth position.

22. The centrifuge of claim 1, further comprising a vibration sensor to detect an imbalance of the carousel during rotation of the carousel.

23. The centrifuge of claim 22, wherein the vibration sensor is to convert a mechanical movement into an electrical signal to detect a location and a magnitude of the imbalance.

24. The centrifuge of claim 22, wherein the vibration sensor comprises a piezoelectric accelerometer.

25. The centrifuge of claim 1, wherein the balancing element is to generate a force vector to counterbalance an imbalance vector associated with the carousel.

26. The centrifuge of claim 25, wherein the force vector is to cancel an imbalance created by the sample tube based on a distance of the first sample tube from an axis of rotation of the carousel.

27. The centrifuge of claim 1, wherein the first sample tube-holding assembly is to slide along a trajectory of the first track.

28. The centrifuge of claim 1, further comprising a brake disposed proximate to a center of the centrifuge to prevent the first sample tube from rotating at a rotational speed of the carousel.

29. The centrifuge of claim 28, wherein the brake comprises a magnetic brake to prevent movement of the first sample tube holder when the first sample tube holder is proximate to the center of the centrifuge.

30. The centrifuge of claim 28, wherein the brake comprises a clamp brake to prevent movement of the first sample tube holder when the first sample tube holder is proximate to the center of the centrifuge.

31. The centrifuge of claim 1, further comprising a protective enclosure surrounding at least a portion of at least one of the first sample tube-holding assembly, the first drive mechanism, or the first movable element.

32. The centrifuge of claim 1, wherein the first sample tube-holding assembly includes a reflector to reflect a signal emitted by an emitter-detector.

33. The centrifuge of claim 32, wherein the reflector is to detect a degree of inclination of the first sample tube-holding assembly.

34. The centrifuge of claim 1, wherein the balancing element comprises an exterior balancing cap and an interior balancing cap, the exterior balancing cap concentric with the interior balancing cap.

35. The centrifuge of claim 34, wherein the exterior balancing cap and the interior balancing cap are to rotate about an axis of rotation of the carousel.

36. The centrifuge of claim 34, further comprising a first motor to rotate the exterior balancing cap.

37. The centrifuge of claim 36, further comprising a second motor to rotate the interior balancing cap.

38. The centrifuge of claim 34, wherein the interior balancing cap comprises:
a first platform to cover the upper portion of the carousel, wherein the first platform is perpendicular to an axis of rotation of the carousel; and
a first skirt perpendicularly coupled to the first platform.

39. The centrifuge of claim 38, wherein the exterior balancing cap comprises:
a second platform to cover the interior balancing cap, wherein the second platform is perpendicular to the axis of rotation of the carousel; and
a second skirt perpendicularly coupled to the second platform.

40. The centrifuge of claim 39,
wherein the interior balancing cap comprises a first portion and a second portion, the first portion comprising the first skirt, the first portion heavier than the second portion, and
wherein the exterior balancing cap comprises a third portion and a fourth portion, the third portion comprising the second skirt, the third portion heavier than the fourth portion.

41. The centrifuge of claim 40, wherein the first portion of the interior balancing cap and the third portion of the exterior balancing cap are separated by 180° when the carousel is in a balanced state.

42. The centrifuge of claim 40, wherein as a position of the first portion of the interior balancing cap changes in relationship to a position of the third portion of the exterior balancing cap, a force vector is created.

43. The centrifuge of claim 40, wherein a first set of bearings is interposed between the upper portion of the carousel and the first platform of the interior balancing cap.

44. The centrifuge of claim 43, wherein a second set of bearings is interposed between the first platform of the interior balancing cap and the second platform of the exterior balancing cap.

45. The centrifuge of claim 44, wherein the second set of bearings is to permit the exterior balancing cap to rotate in a first plane above a second plane of the first platform of the interior balancing cap.

46. The centrifuge of claim 45, wherein the first set of bearings is to permit the interior balancing cap to rotate in the second plane above the upper portion of the carousel.

47. The centrifuge of claim 1, wherein the first drive mechanism comprises a lead screw.

48. The centrifuge of claim 1, wherein the first movable element comprises a lead screw nut.

49. The centrifuge of claim 48, wherein the first sample tube-holding assembly is coupled to the lead screw nut by a torsion spring.

50. The centrifuge of claim 49, wherein the torsion spring biases the first sample tube-holding assembly to a vertical position and a centrifugal force counteracts a force of the torsion spring as the first sample tube-holding assembly moves away from a center of the centrifuge.

51. The centrifuge of claim 1, further comprising a torsion spring and a vertical hinge, the torsion spring and the vertical hinge to jointly control a door, the door to permit access to the first sample tube-holding assembly.

52. The centrifuge of claim 1, wherein the balancing element comprises a balancing weight.

53. The centrifuge of claim 52, wherein the balancing weight is coupled to a first positioning mechanism.

54. The centrifuge of claim 53, further comprising a third drive mechanism to control the first positioning mechanism.

55. The centrifuge of claim 54, wherein the third drive mechanism is to move the balancing weight via a first lead screw.

56. The centrifuge of claim 55, further comprising a fourth drive mechanism to move the balancing weight via a second lead screw.

57. The centrifuge of claim 56, wherein the balancing weight is to be moved in a first direction via the third drive mechanism and a second direction via the fourth drive mechanism, the first direction perpendicular to the second direction.

58. The centrifuge of claim 57, wherein the balancing weight is to be moved in the first direction and the second direction to negate an imbalance vector generated by the carousel during rotation of the carousel.

59. The centrifuge of claim 53, further comprising a second positioning mechanism, the first positioning mechanism communicatively coupled to the second positioning mechanism.

60. The centrifuge of claim 59, wherein the first positioning mechanism comprises a first ball bearing and the second positioning mechanism comprises a second ball bearing perpendicular to the first ball bearing.

61. The centrifuge of claim 59, further comprising a connector interposed between the first positioning mechanism and the second positioning mechanism, the connector to connect the first positioning mechanism and the second positioning mechanism.

62. The centrifuge of claim 1, wherein the balancing element comprises at least a first balancing element movable by a third drive mechanism and a second balancing element movable by a fourth drive mechanism.

63. The centrifuge of claim 1, wherein a weight of the carousel exceeds a combined weight of the first sample tube and the first sample tube holder.

64. The centrifuge of claim 1, further comprising field coils mounted to the lower portion of the carousel.

65. The centrifuge of claim 1, wherein the carousel is to wirelessly communicate with external controllers.

66. The centrifuge of claim 1, wherein power is provided from a source external to the carousel.

* * * * *